(12) United States Patent
Lowe et al.

(10) Patent No.: US 7,223,988 B2
(45) Date of Patent: May 29, 2007

(54) COLOR TUNABLE PHOTOLUMINESCENT BLENDS

(75) Inventors: Christiane Lowe, Wallisellen (CH); Christoph Weder, Shaker Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 10/517,897

(22) PCT Filed: Jun. 20, 2003

(86) PCT No.: PCT/US03/19532

§ 371 (c)(1),
(2), (4) Date: Dec. 29, 2005

(87) PCT Pub. No.: WO04/000970

PCT Pub. Date: Dec. 31, 2003

(65) Prior Publication Data

US 2006/0108564 A1  May 25, 2006

Related U.S. Application Data

(60) Provisional application No. 60/390,627, filed on Jun. 21, 2002.

(51) Int. Cl.
*H05B 33/00* (2006.01)
*C09K 11/06* (2006.01)
*C07C 255/00* (2006.01)
*C07C 205/00* (2006.01)
*C07C 43/11* (2006.01)

(52) U.S. Cl. ............... 250/484.4; 252/301.16; 430/139; 558/402; 558/410; 568/586; 568/609

(58) Field of Classification Search ............... 558/402, 558/410; 568/586, 609; 430/139; 252/301.6, 252/301.16; 313/504; 250/484.4
See application file for complete search history.

(56) References Cited

U.S. PATENT DOCUMENTS

| 5,328,809 A | 7/1994 | Holmes et al. |
| 6,127,693 A | 10/2000 | Chen et al. |
| 6,235,414 B1 * | 5/2001 | Epstein et al. ............... 428/690 |
| 6,368,732 B1 | 4/2002 | Jin et al. |

FOREIGN PATENT DOCUMENTS

WO    WO 98/41065    9/1998

* cited by examiner

*Primary Examiner*—Richard L. Schilling
(74) *Attorney, Agent, or Firm*—Kirkpatrick & Lockhart Preston Gates Ellis LLP

(57) ABSTRACT

Embodiments of the present invention are directed toward a photoluminescent article comprising at least one host material and at least one color tunable photoluminescent dye. In certain embodiments, the emission spectrum of the at least one tunable photoluminescent dye may be dependent on the supramolecular architecture of the material. The photoluminescent emission spectrum of the dye is capable of being shifted by subjecting the article to an external stimuli such as, but not limited to, a mechanical deformation, a temperature change, aging of the article, a pressure change, exposure to a chemical compound. In specific embodiments, the color tunable photoluminescent dye is an oligo(phenylene vinylene) compound, such as, but not limited to, 1,4-Bis-(α-cyano-4-methoxystyryl)-benzene, 1,4-bis-(α-cyano-4-methoxystyryl)-2,5-dimethoxybenzene, and 1,4-bis-(α-cyano-4-(2-ethylhexyloxystyryl)-2,5-dimethoxybenzene and 2,5-bis-(α-cyano-4-methoxystyryl)-thiophene. A further embodiment of the invention is method of determining a degree of mechanical deformation, a temperature change, aging of the article, a pressure change, exposure to a chemical compound on an article.

27 Claims, 26 Drawing Sheets

COLOR TUNABLE PHOTOLUMINESCENT BLENDS

CROSS-REFERENCE TO RELATED APPLICATIONS

The present application is based on International Application No. PCT/US2003/019532 filed 20 Jun. 2003, published as International Publication Number of WO 2004/000970 A1 on Dec. 31, 2003, that claims priority from U.S. Provisional Application No. 60/390,627 filed on Jun. 21, 2002.

BACKGROUND

The use of photoluminescent polymers has attracted significant interest. The potential use of π-conjugated semiconducting polymers in light emitting diodes holds a great potential. Semiconducting polymers combine the processability and outstanding mechanical properties of polymers with the exceptional, readily tailored electronic and optical properties of functional organic molecules.

Poly(phenylenevinylenes) ("PPV's") represent the most extensively studied class of π-conjugated semi-conducting polymers. Research on these polymers has shown that the molecular and supramolecular architectures of the PPV's affect their electronic properties. Various examples have been shown that the properties may be tailored to many different applications.

A number of low molecular weight oligo(p-phenylenevinylene) derivatives ("OPVs") have also recently been investigated. The electronic properties of the OPV's have served as models for the corresponding PPV derivative. The substitution of OPV's has resulted in a bathochromatic shift of their emission spectra.

The emission characteristics of the OPV's strongly depend on the state of the matter. Bathochromatic shifts of up to 100 nm have been reported between the emission of the crystalline solid with the emission of a low viscosity molecular solution of the OPV. It has been suggested that the strong π-π overlap encounter in the lattice of the crystalline solid results in the bathochromatic shift. The pronounced π-π interactions cause multiple conjugated molecules to adopt a 'sandwich structure' and arrange under cofacial π-π stacking with distances between the planes of the conjugated systems in the order of 3-4'. This supramolecular architecture leads to the formation of excimers that may exhibit strongly red shifted fluorescence bands and long fluorescence lifetimes.

SUMMARY

Embodiments of the present invention are directed toward a photoluminescent article comprising at least one host material and at least one color tunable photoluminescent dye. In certain embodiments, the emission spectrum of the at least one tunable photoluminescent dye is dependent on the supramolecular architecture of the material. The photoluminescent emission spectrum of the dye is capable of being shifted by subjecting the article to an external stimuli such as, but not limited to, a mechanical deformation, a temperature change, aging of the article, a pressure change, exposure to a chemical compound. In specific embodiments, the color tunable photoluminescent dye is an oligo(phenylene vinylene) compound, such as, but not limited to, 1,4-Bis-(α-cyano-4-methoxystyryl)-benzene, 1,4-bis-(α-cyano-4-methoxystyryl)-2,5-dimethoxybenzene, and 1,4-bis-(α-cyano-4-(2-ethylhexyloxystyryl) )-2,5-dimethoxybenzene and 2,5-bis-(α-cyano-4-methoxystyryl)-thiophene.

A further embodiment of the invention is method of determining a degree of mechanical deformation, a temperature change, aging of the article, a pressure change, exposure to a chemical compound on an article. The method comprises measuring the photoluminescent emission spectra of an article comprising at least one host material and at least one color tunable photoluminescent dye, wherein the emission spectrum of the at least one tunable photoluminescent dye is dependent on the supramolecular architecture of the material; and comparing the photoluminescent emission spectrum of the article with the photoluminescent emission spectrum prior to the mechanical deformation, a temperature change, aging of the article, a pressure change, exposure to a chemical compound.

DESCRIPTION OF THE FIGURES

(FIGS. 8A and 8C) and toluene at 70° C. (FIGS. 8B and 8D), respectively, wherein the concentration of BCMDB in the dyeing solution was varied between 1, 5, 10, and 20 mg/mL.

FIGS. 9A-9C are PL emission spectra of blend films of LLDPE and BCMDB as a function of draw ratio in tensile-oriented films (FIGS. 9A and 9B) and annealing (FIG. 9C), wherein FIG. 9A shows spectra of a film based on LLDPE containing 1.2% octene co-monomer, FIG. 9B shows spectra of a film based on LLDPE containing 9.3% octene co-monomer and FIG. 9C shows spectra of a film based on LLDPE containing 1.2% octene co-monomer, wherein the sample was annealed at 85° C. before quenching the sample to room temperature and recording the PL spectrum;

(FIG. 13A), 140° C. (FIG. 13B), and 100° C. (FIG. 13C);

DESCRIPTION OF EMBODIMENTS OF THE INVENTION

Figure 1:
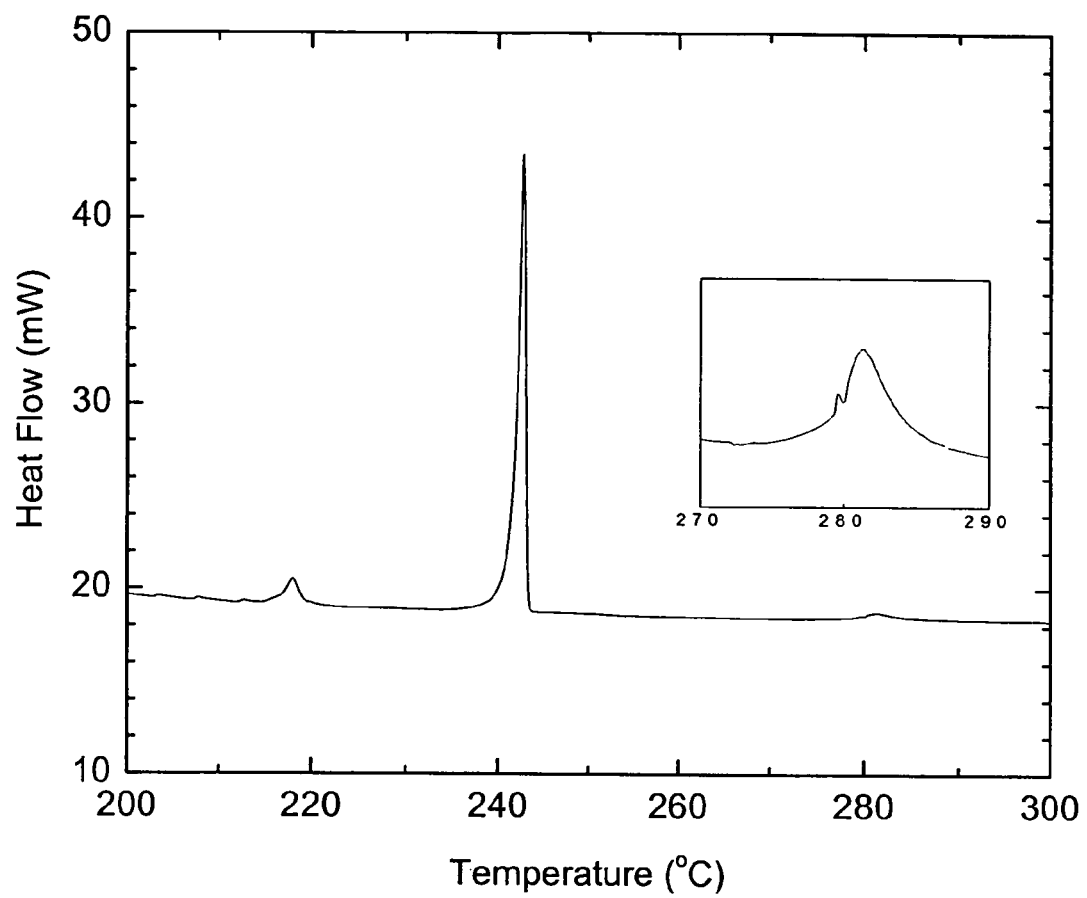
FIG. 1 is a graph of the output of a differential scanning colorimetric measurement of BCMB at heating and cooling rates of 5 K/min, the inset is an enlargement of the curve between 270° C. and 290° C.

The invention relates to a photoluminescent article comprising a host, such as a, polymer and a color tunable photoluminescent dye. A color tunable photoluminescent dye may be any dye that is capable of emitting a different emission spectrum based upon the state of matter or the environment to which the dye has been exposed. The dye may be, for example, a dye that forms excimers that emit a different emission spectrum based upon the relative concentration of the excimers to monomers or a dye that emits a different spectrum based upon the supramolecular relationship between the dye and the host polymer, other dye molecules or another chemical compound in the material or article. Supramolecular architecture of a material broadly refers to the relationship of the components of the material concerning their intermolecular bonding, relative arrangement towards each other, and the structures and functions of the entities formed by the association and/or arrangement of two or more chemical species. An intermolecular bond is a general term that includes ion pairing (electrostatic), hydrophobic and hydrophilic interactions, hydrogen-bonding, host-guest interactions, pi-stacking, coordination, and Van der Walls interactions, as well as other intermolecular interactions. Additionally, the term 'monomer' is used herein to describe single-molecule excited states, as opposed to excimers. For instance, in one embodiment, the pronounced π-π interactions encountered in the crystalline lattice of the planar, conjugated, photoluminescent ("PL") molecules may lead to the formation of excimers. As a result, the emission characteristics of these molecules may strongly depend on their supramolecular architecture. Embodiments of the present invention comprise controlling the emission color of a given PL dye over a wide range by merely tuning the extent of π stacking between the limiting states of crystalline solid and molecular liquid solution. For use in the present invention, a maximum of the emission spectrum of the color tunable photoluminescent dye for the crystalline solid to a maximum of the emission spectrum for the molecular liquid solution may shift any measurable amount. Preferably, a maximum of the spectra shifts greater than 50 nm, more preferably, the shift is greater than 75 nm. For certain embodiments, such as, where visible inspection of the shift in the emission spectra is desired, a shift in the spectra of at least 100 nm may be desired or, more preferably, a shift of at least 125 nm is desired.

For example, the emission spectrum of a color tunable photoluminescent dye in the host material or article depends on several factors, such as, the concentration of dye, the solubility of the dye in the host, such as a polymer, the polarity of the host, the ability of a dye to form aggregates or excimers, the degree of bathochromatic shift of the dye excimers relative to the monomers, the degree of exposure to heat, external pressure applied to the article or material and the degree of work the article or material has experienced, as well as other factors of particular interest to certain applications, is the ability to change the emission spectrum of an article or material based in a mechanical deformation. Therefore, a shift in the emission spectrum of the article or material may occur if the article or material is subjected to mechanical deformation, a temperature change, aging of the article or material, a pressure change, or an environmental change, such as exposure to a chemical compound, as well as other factors.

The emission spectrum appears to depend on the chemical and physical interactions of the dye molecules with other compounds in the host material. These interactions may include dye molecule to dye molecule interactions, dye molecule to polymer molecule interactions or dye molecule to other compounds in the host material. For example, excimer formation of the dye in the polymer may cause a large bathochromatic shift in the emission spectrum of the article. Subsequent annealing or cold working, as well as other forces and factors, may reduce the number of excimers in the polymer and therefore shift the emission spectrum more toward that of the dilute solution of the dye. Other factors may increase the number of excimers in the polymer and result in a shift of the spectrum more toward the spectrum of the crystalline solid. The segregation and aggregation of the dye in the host material may be reversible or irreversible. For embodiments of the present invention, the ratio of the photoluminescence intensity of the excimer portion to the photoluminescence intensity of the monomer portion, or the portion not in an excimer, may be changed by any measurable amount, however, in certain embodiments a change in this ratio by a factor of at least 3 may be preferred, in certain other embodiments, a change in this ratio by a factor of at least 4 may be preferred, and more preferably by a factor of at least 5, and most preferably by a factor of at least 7. The change in the ratio of the photoluminescence intensity of the excimer portion to the photoluminescence intensity of the monomer portion may depend on the type of external stimuli exerted upon the embodiment, such as, mechanical deformation, temperature change, aging of the article, pressure change, or exposure to chemical compound.

The host material according to the present invention may be any natural or synthetic solid, or high-viscosity fluid, which allows adequate incorporation of the color tunable dye and allows segregation and aggregation of the color tunable dye, such as, for example, natural polymers, low molecular inorganic and organic materials, synthetic polymers, including, but not limited to, polyolefins such as polyethylenes (including linear low density polyethylene, low density polyethylene, high density polyethylene, ultra high molecular weight polyethylene) and poly(propylene), cyclic olefin polymers and copolymers, poly(acrylate)s such as polymethyl methacrylate, poly methacrylate, polybutyl acrylate, poly(acrylamide), poly(acrylonitrile), vinyl polymers, such as poly(vinylchloride), poly(vinylidenechloride), poly(vinylfluoride), poly(tetrafluoroethylene), poly(chlorotrifluoroethylene), poly(vinylacetate), poly(vinylalcohol), poly(2-vinylpyridine), poly(vinyl butyral), poly(styrene)s, copolymers such as acrylonitrile butadiene styrene copolymer, ethylene vinyl acetate copolymers, polyamides, such as polyamide 6 and 6,6, polyamide 12, polyamide 4,6, polyesters, such as poly(ethylene terephthalate), poly(butylene terephthalate), and poly(ethylene naphthalate), poly(carbonate)s, polyurethanes, poly(aryl sulfones), poly(phenyleneoxide), thermoset resins such as phenol formaldehyde resins (resoles, novolacs), epoxy resins, regenerated cellulose, such as cellophane, cellulose acetate, cellulose acetate butyrate, natural fibers such as wool, silk, cotton, ramie, jute., starch-based materials, etc., as well as blends or composites comprising two or more of the heretofore mentioned or other compounds. Additionally, the host material may be an elastomer, such as, styrene-butadiene copolymers, polybutadiene, ethylene-propylene copolymers, polychloroprene, polyisoprene, nitrile rubbers, silicone rubbers, thermoplastic elastomers. The properties and functionality incorporated in the host material may be chosen such that the solubility and diffusion characteristics of the dye in the host material meet the desired application. These properties such as the degree of branching, the length of branching, molecular weight, polarity, functionality, as well as other properties may be used to vary the rate or degree of bathochromatic shift of the emission spectrum based upon the degree of external stimulation the article or material experiences.

The dye may be any photoluminescent dye, which results in a shift in emission spectrum based on the external stimulation, including, but not limited to, planar aromatic compounds such as naphthalene, pyrene, anthracene, phenanthrene and their derivatives such as 2,6-naphthalenedicarboxylate, and 1,3-dipyrenylpropane; conjugated polymers such as poly(9,9-dioctylfluorene) and poly(3-methyl-4-octyl-thiophene) and their constituent moieties such as 9-phenylfluorene, as well as oligomers thereof; planar conjugated molecules with electron withdrawing groups such as p,p'-diformyl-trans,trans,trans-1,6-diphenyl-1,3,5-hexatriene, substituted perylenes such as bis(neopentylimido) perylene, and oligo(phenylene vinylene)s (OPVs). For example, a new family of PL dyes that exhibit bathochromic shifts up to 138 nm when comparing the PL emission of a dilute solution with that of the crystalline dye. This family includes OPV's, such as 1,4-bis-(α-cyano-4-methoxystyryl)-benzene ("BCMB"), 1,4-bis-(α-cyano-4-methoxystyryl)-2,5-dimethoxybenzene ("BCMDB"), and 1,4-bis-(α-cyano-4-(2-ethylhexyloxystyryl)-2,5-dimethoxybenzene ("BCEDB"). Generally the family may include compound of the general formula:

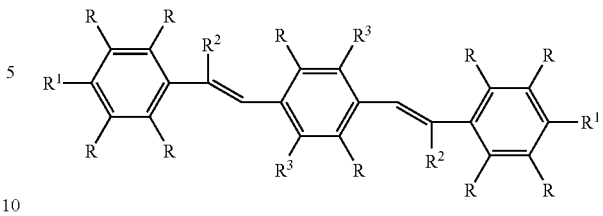

where $R^2$ may be any group which affects the desired physical or electronic properties of the compound, but preferably is an electron withdrawing group, such as, but not limited to, cyano, halogen, Cl, F, Br, $C(=O)R$, $C(=O)OR$, $C(=O)NR_2$, $CF_3$, CN, $S(O)_2OH$, $NO_2$, and $N^+R_4$; R, $R^1$, and $R^3$ may be any group which affects the desired physical or electronic properties of the compound, such as, but not limited to H, straight chain, branched or cyclic saturated alkyl, alkenyl, or alkynyl, hydroxy alkyl, alkyloxy, carboxy alkyl, aryl, or substituted aryl.

The exemplary OPVs, BCMD, BCMDB, and BCEDB are highly photoluminescent, and the comparison of the emission spectra of the crystalline solids with the ones of the corresponding low-viscosity molecular solutions reveals, particularly in case of BCMDB, an extremely large bathochromic shift. Without limiting the invention with a discussion of the mechanism of the bathochromatic shift, this effect is consistent with the formation of excimers that are characterized by low-bandgap emission.

Literally any combination of monomer and excimer can be achieved by changing the phase behavior of the blends or mixtures of host material and PL dye via composition, processing conditions, or temperature. Mechanical deformation leads to a substantial change of the emission characteristics of such blends. This effect appears to bear significant potential for technological applications, in particular the use of such dyes and blends comprising such dyes as integrated strain sensors, failure indicators, chemical sensors, as well as tamper resistant films, identification marks, authenticity proofs, and other security features in polymer objects. The blends of host polymeric material and PL dye may be produced via a variety of standard techniques, for example, but not limited to, conventional melt blending, diffusion of the dye from a solution into a polymer object, or forming the polymer in the presence of the dye. As noted heretofore, color-tunable dye and host material can be different species, but they might also be combined in one. To combine dye and host material, the moieties may be covalently linked by adequate chemical bonds. The combination of the dye and a polymer can, for example, be achieved by attaching the dye, possibly via an adequate spacer, as a side chain. The dye can also be incorporated into the polymer backbone.

The article may comprise additional compounds, such as, solvents, processing aids, viscosity modifiers, UV inhibitors, color additives, as well as other additives. A solvent is not necessary in the embodiments of the invention, however, when a solvent is used, suitable solvents include ethers, cyclic ethers, $C_5$-$C_{10}$ alkanes, $C_5$-$C_8$ cycloalkanes which may be substituted with from 1 to 3 $C_1$-$C_4$ alkyl groups, aromatic hydrocarbon solvents, such as toluene, halogenated hydrocarbon solvents, such as trichloromethane, acetonitrile, dimethylformamide, mixtures of such solvents, and supercritical solvents (such as $CO_2$, $C_1$-$C_4$ alkanes in which any H may be replaced with F, etc.). Suitable ethers include compounds of the formula $R_4OR_5$, in which each of $R_4$ and $R_5$ is independently an alkyl group of from 1 to 6 carbon atoms which may be further substituted with a $C_1$-$C_4$-alkoxy group. Preferably, when one of $R_4$ and $R_5$ is methyl, the other of $R_4$ and $R_5$ is alkyl of from 4 to 6 carbon atoms or $C_1$-$C_4$-alkoxyethyl. Examples include diethyl ether, diphenyl ether, ethyl propyl ether, dipropyl ether, methyl t-butyl ether, di-t-butyl ether, dimethoxyethane, diethylene glycol dimethyl ether, as well as other ethers. Suitable cyclic ethers include THF and dioxane. Suitable aromatic hydrocarbon solvents include benzene, toluene, o-xylene, m-xylene, p-xylene and any isomer or mixture of isomers of cumene. Suitable halogenated hydrocarbon solvents include $CH_2Cl_2$, $CHCl_3$, 1,2-dichloroethane and benzene substituted from 1 to 6 times with fluorine and/or chlorine.

Unless otherwise indicated, all numbers expressing quantities of ingredients, composition, time, temperatures, and so forth used in the present specification and claims are to be understood as being modified in all instances by the term "about." Accordingly, unless indicated to the contrary, the numerical parameters set forth in the specification and claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, may inherently contain certain errors necessarily resulting from the standard deviation found in their respective testing measurements. Unless otherwise indicated, all numbers expressing dye concentrations are given in weight percent.

Preparation of Testing of Exemplary PL Dyes

BCMB, BCMDB, and BCEDB were synthesized through the Knoevenagel reaction. As shown in Scheme 1, BCMB and BCMDB were synthesized by the reaction of (4-methoxyphenyl)acetonitrile with terephthaldicarboxyaldehyde and 2,5-dimethoxy terephthaldicarboxyaldehyde, respectively. BCEDB was prepared by a similar reaction between (4-(2-ethylhexyloxy)phenyl)acetonitrile and 2,5-dimethoxy-terephthaldehyde. The experimental conditions relied on a mixture of THF and t-BuOH as the solvent, and minor amounts of n-$Bu_4NH_4OH$ and anhydrous t-BuOH. BCMB, BCMDB, and BCEDB precipitated from the reaction mixture and were obtained in high yield (90, 89, and 70%, respectively) and analytically pure form, as evidenced by $^1H$ NMR and elemental analysis data.

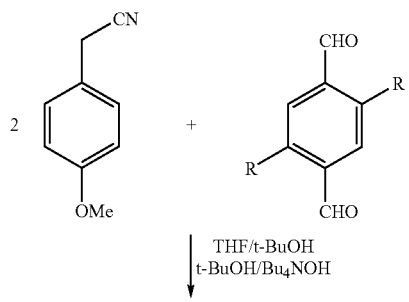

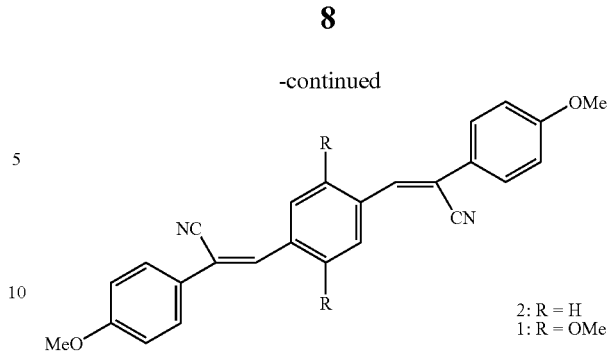

Scheme 1: Synthesis of 1,4-bis-(α-cyano-4-methoxystyryl)-benzene (2, R═H) and 1,4-bis-(α-cyano-4-methoxystyryl)-2,5-dimethoxybenzene (1, R═OMe) by Knoevenagel reaction.

Figure 2A:
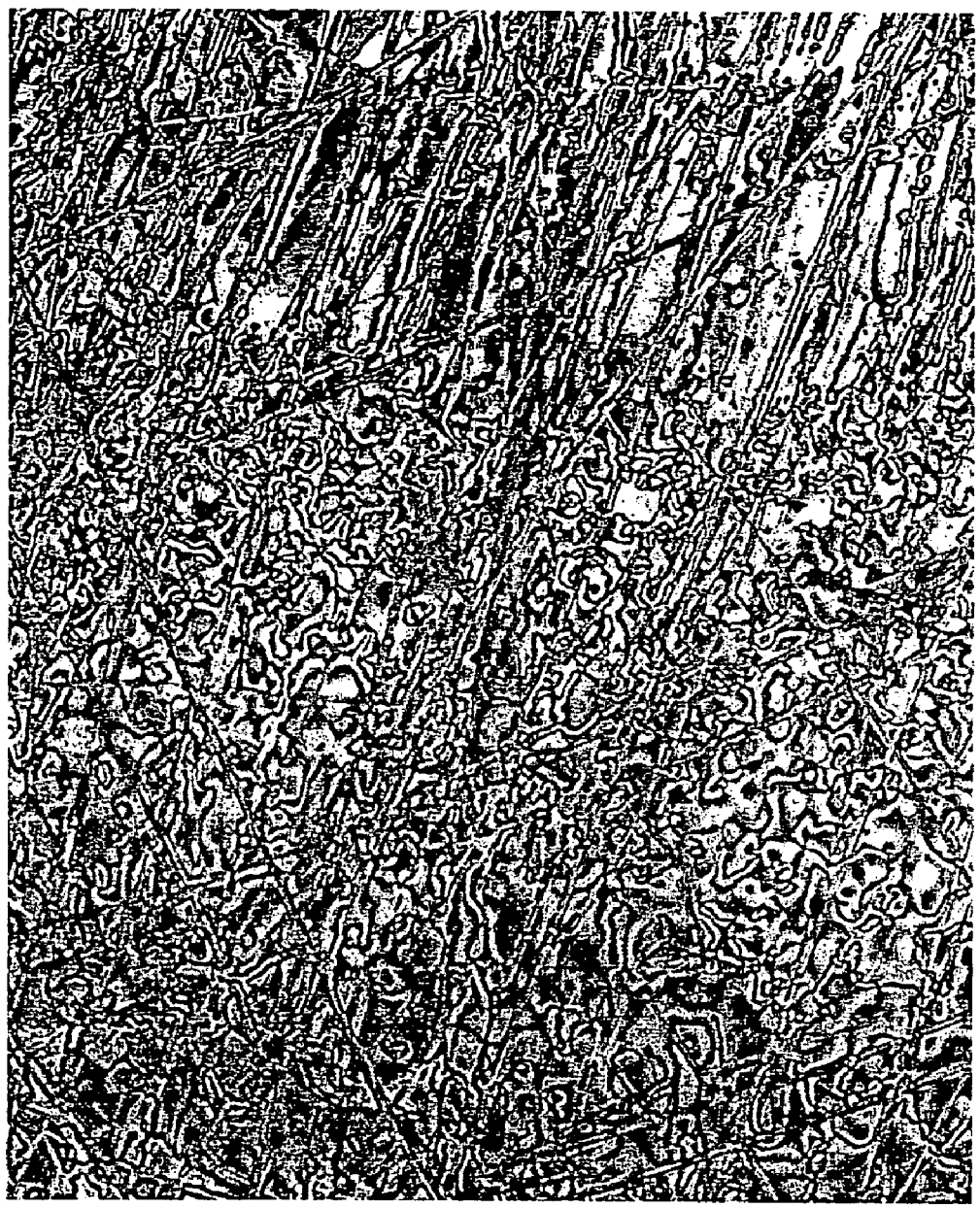
FIG. 2A is a polarized optical microscopy (crossed polarizers) image of BCMB in the smectic phase that occurs at approximately 260° C.
Figure 2B:
FIG. 2B is a polarized optical microscopy (crossed polarizers) image of BCMB in the nematic phase that occurs at approximately 275° C.

The thermal properties of BCMB and BCMDB were studied using differential scanning calorimetric (DSC) measurements at heating and cooling rates of 5 K/min, as well as polarized optical microscopy. Upon heating, the DSC trace of BCMB displayed a weak (ΔH=9.7 J/g) irreversible endothermic transition at 220° C. and reversible endothermic transitions at 245 (ΔH=109.4 J/g) and around 281 (ΔH=2.5 J/g) ° C. (FIG. 1). As can be seen from the inset in FIG. 1, the latter transition is superimposed by a weak reversible transition around 279.5° C. The features of the DSC spectrum remained essentially unchanged in subsequent heating cycles, except that, as mentioned above, the transition at 220° C. and disappeared, and the position of the peaks exhibited minor changes; for example, in the third heating scan the transitions, in ° C., are K 237 S 274 N 279 I. A detailed investigation with polarization microscopy revealed no changes when passing 220° C., suggesting that the transition observed by DSC at this temperature is most likely a crystal-crystal transition. Gratifyingly, all other transitions determined by DSC were also observed by optical microscopy, and the transition temperatures determined by these two methods were found to correlate well. Polarization microscopy revealed that BCMB enters a birefringent, highly viscous, mobile state around 243° C. The texture suggests the presence of a smectic mesophase, which is also consistent with the large ΔH associated with the transition and the spherulitic growth pattern observed upon cooling. Another transition to a highly mobile birefringent phase was observed around 272° C., before the isotropic melt was entered around 278° C. See FIGS. 2A and 2B. The low viscosity and the Schlieren texture of the phase between 272 and 278° C. (DSC: 279.5-281° C.) points to a nematic phase in this extremely narrow temperature regime BCMDB, by contrast, displayed only one well-defined, reversible transition at 248° C. (ΔH=101.2 J/g), which by means of polarization microscopy could be assigned to the crystalline-isotropic transition. Thus, it appears that the introduction of two methoxy groups into the central ring of the system reduces the molecular aspect ratio sufficiently to frustrate the onset of liquid crystallinity.

Photoluminescence of the Exemplary PL Dyes

Figure 3:
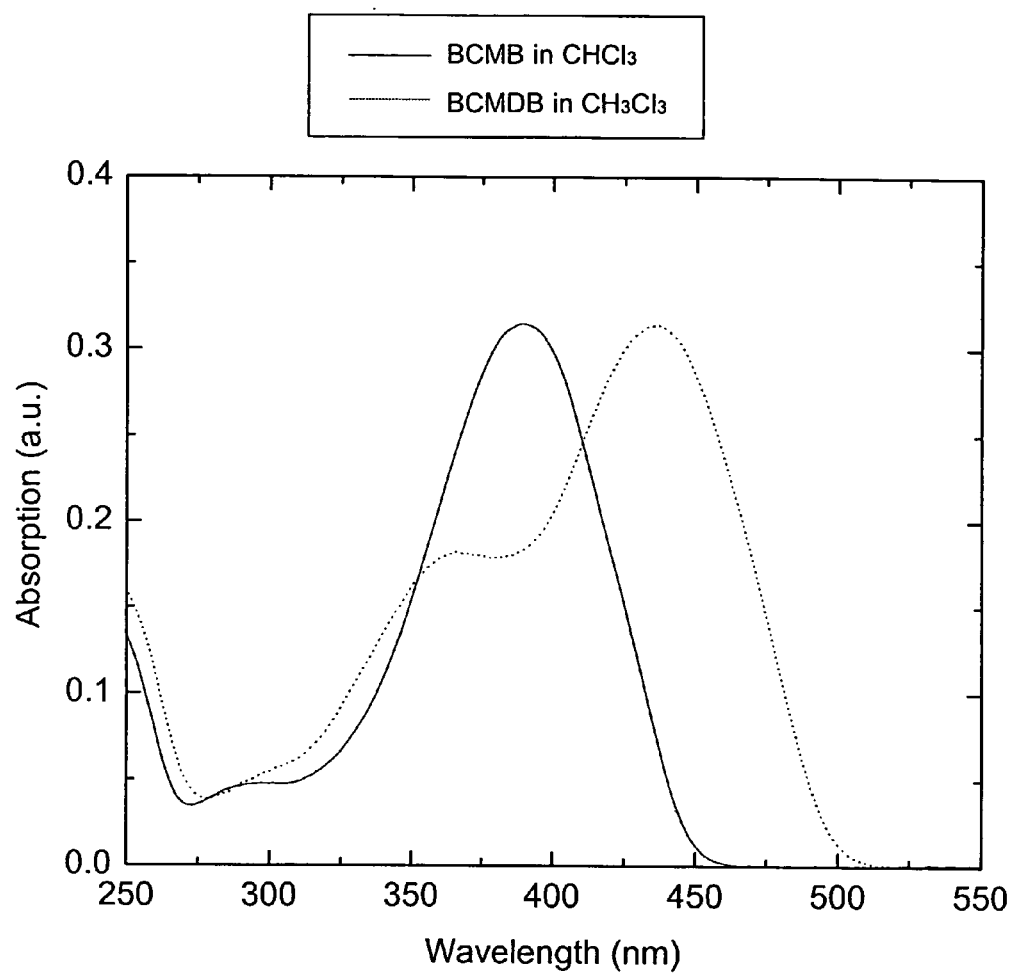
FIG. 3 is a graph of the UV-vis absorption spectra for BCMB in $CHCl_3$ and BCMDB in $CHCl_3$ solution.

The OPV derivatives may be bright yellow, such as BCMB, or orange, such as BCMDB and BCEDB, and the compounds are strongly photoluminescent powders. The optical properties of these exemplary dyes were studied in detail by UV-Vis absorption and steady-state PL spectroscopy in different states of matter. FIG. 3 shows the UV-Vis absorption spectra of BCMB and BCMDB in $CHCL_3$ solution. Compound BCMB displays an absorption band with a maximum at 389 nm and a weak shoulder around 290 nm. As expected, the introduction of the methoxy groups into the central ring of BCMDB caused a noticeable bathochromic shift in the absorption of BCMDB which features a maximum at 436 nm and a pronounced shoulder around 365 nm. BCEDB displays an absorption maximum at 440 nm, and a pronounced shoulder at 371 nm.

Figure 4:
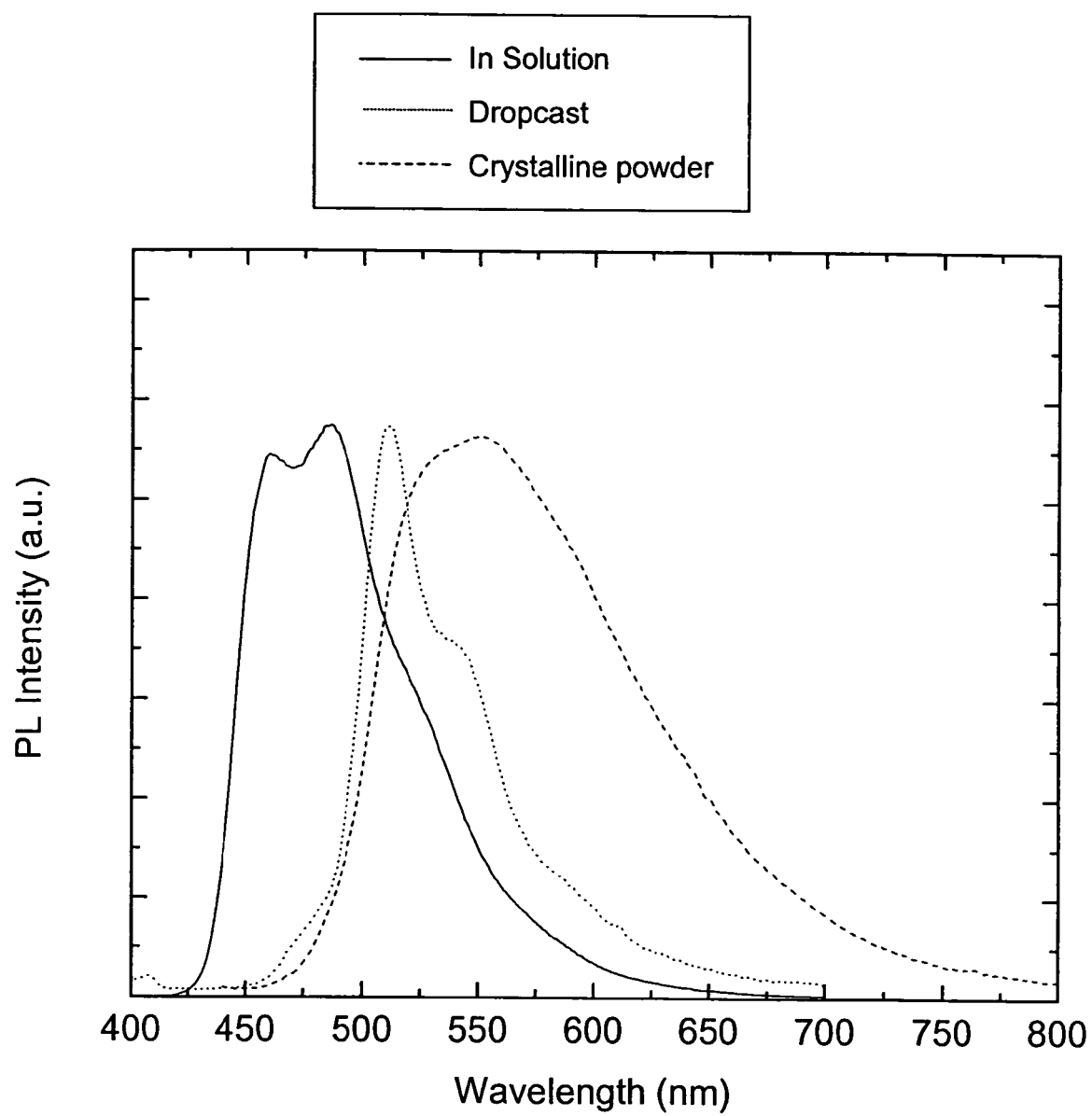
FIG. 4 is a graph of the photoluminescent intensity curve of BCMB in solution, as drop cast and in a crystalline powder.
Figure 5:
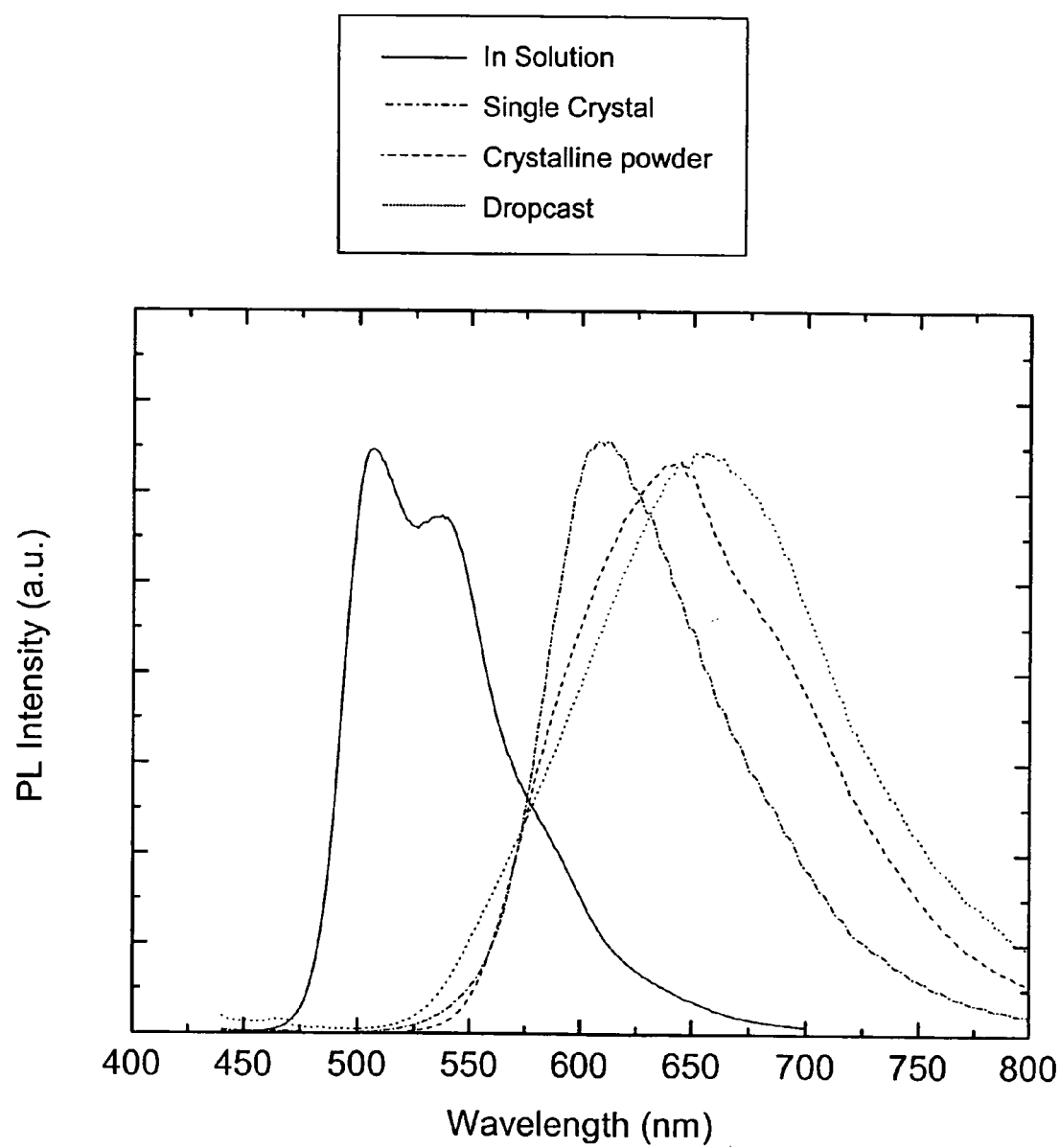
FIG. 5 is a graph of the photoluminescent intensity curves of BCMDB in solution, as a single crystal, as drop cast and in a crystalline powder.

PL spectra of BCMB and BCMDB in solution and various solid states are shown in FIGS. 4 and 5. In solution, BCMB shows an emission band that ranges from approximately 425 to 650 nm and exhibits two well-resolved maxima at 461 and 486 nm (FIG. 4). In contrast to the absorption spectrum, the emission spectrum of the solution is clearly vibrationally structured, indicating a better planarization of the conjugated system in the emitting state than in the electronic ground state. The "as-synthesized", (semi)crystalline powder of BCMB displays a much broader emission band than the solution with a maximum at 550 nm (FIG. 4). The substantial red shift (64-89 nm) and the fact that the vibronic structure of the emission band has disappeared seem to suggest that the emission of this dye in the solid state is indeed predominantly governed by excimers rather than single-molecule or monomer emission. Interestingly, the PL spectrum of a drop-cast film of BCMB represents an intermediate between the emission in solution and the solid state (FIG. 4). The spectrum of the drop cast solid is fairly narrow and vibrationally structured, with maxima at 513 and 536 nm, indicating that, in this case, the contribution from a disordered fraction is dominant. This finding is consistent with the rapid solidification of the host material, which may be caused by the high vapor pressure of the casting solvent employed and the limited solubility of BCMB, presumably leading to a poorly ordered solid state.

The solution PL spectrum of BCMDB shows similar features as the one of BCMB. See FIG. 5. The emission band of BCMDB in solution is slightly red-shifted when compared to BCMB, with maxima at 506 and 538 nm. The emission spectrum of the "as-synthesized", (semi)crystalline powder extends from approximately 530 to >800 nm and features a maximum around 644 nm. The fact that the spectrum of the crystalline material is broad and featureless, and the extraordinarily large bathochomic shift of 106-138 nm are again consistent with excimer formation in the crystalline lattice of this material. FIG. 5 also includes the PL intensity curves for a drop-cast film, and single crystals of BCMDB. The spectrum of the drop-cast film is rather similar to the one of the crystalline powder and displays a maximum at 654 nm. This finding seems to suggest that a rather efficient co-facial $\pi$-stacking of the chromophores is achieved, even if the dye is solidified from a rapidly evaporating solvent. The PL emission spectrum of the single crystals displays a maximum at 612 nm, thus, slightly blue-shifted compared to the spectra of the other solid samples of BCMB investigated here. This result points to a less pronounced $\pi$-$\pi$ overlap in the single crystal. The PL emission characteristics of BCEDB in solution are similar to those of BCMDB. BCEDB displays PL maxima at 508 and 541 nm. The "as synthesized" crystalline solid displays a PL spectrum with maximum around 619 nm.

Figure 6:
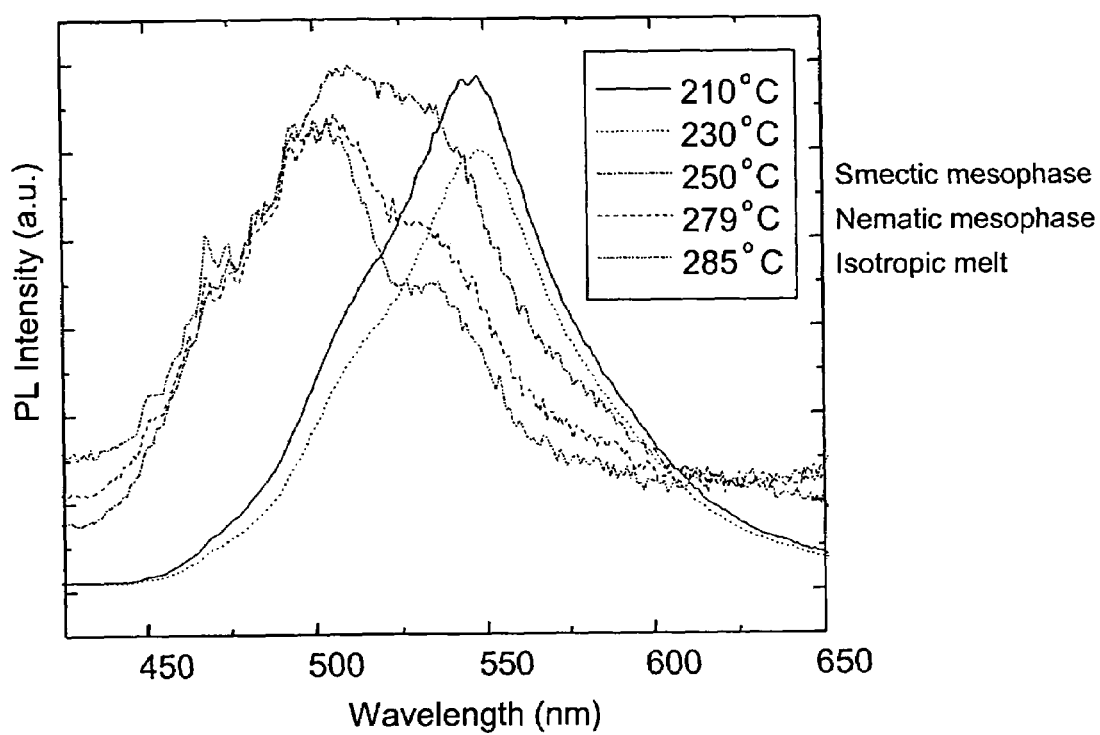
FIG. 6 is a graph of the PL emission spectra of BCMB as a function of temperature wherein the intensities of the spectra were scaled to fit the graph, however, the absolute intensities of the mobile phases at temperatures above 230° C. were reduced by a factor of approximately 25 as compared to the solid state.

BCMB displays liquid-crystalline behaviour. As can be seen from FIG. 6, the spectral characteristics of the emission of the liquid crystal are essentially unchanged when comparing spectra of the "as-synthesized" powder recorded at 210 and 230° C. (i.e., at temperatures slightly below and above the solid-solid transition observed for this material) with the one of the room-temperature sample. See FIG. 4. The emission maximum remains at 550 nm, but the high-temperature spectra are somewhat narrower than the room-temperature spectrum. The PL emission characteristics experience a significant change when the material enters the smectic mesophase. See FIG. 6, spectrum recorded at 250° C. The maximum of PL emission spectrum shifts to 511° C., concomitant with the fact that the intermolecular $\pi$-$\pi$ interactions are substantially reduced and that emission from individual molecules is the dominant radiative process. Consistent with this interpretation, the emission characteristics of the sample remained essentially unchanged when entering the nematic mesophase and the isotropic melt, respectively (spectra recorded at 279 and 285° C., of FIG. 6). It should be noted that (although not reflected by FIG. 6, which shows arbitrary PL intensities) the PL intensity of the mobile phases (>230° C.) were reduced by a factor of approximately 25 when compared to the solid state, which is consistent with the possibility for non-radiative relaxation processes under high-temperature/high-mobility conditions.

Photoluminescent Articles and Materials

Figure 7:
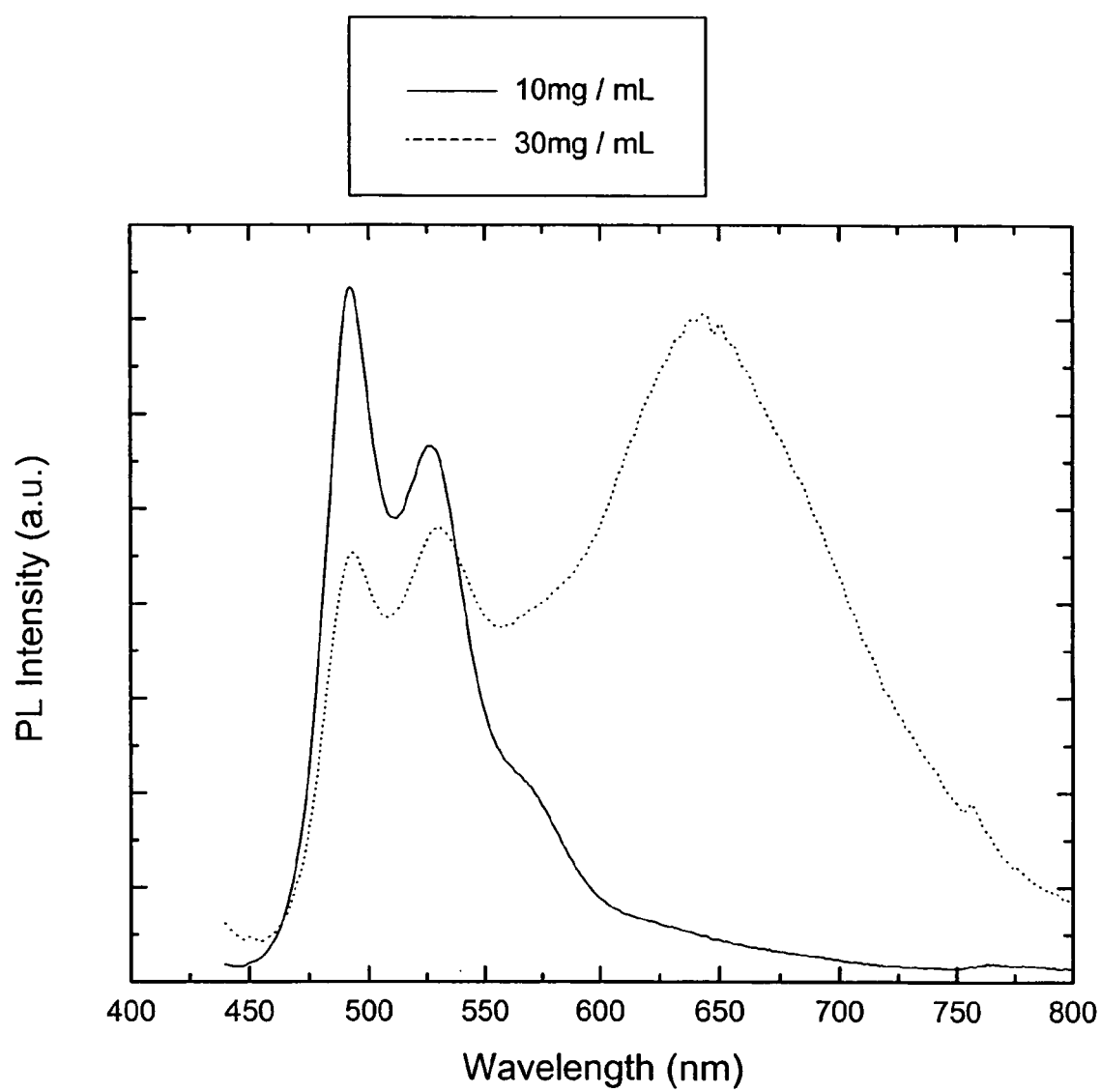
FIG. 7 is a graph of the photoluminescent intensity curves of an isotactic polypropylene film swelled by a 10 mg/mL solution of BCMDB in $CHCl_3$ for about 16 hours at room temperature ~10 mg/mL and a 30 mg/mL solution of BCMDB in $CHCl_3$ for about 3 hours at 60° C.

A wide variety of materials compositions can be envisioned according to the present invention. These materials may be formed into a variety of shapes, including, but not limited to, films, sheets, plates, 3-dimensional objects including for example automotive and airplane parts, toys, household goods, coatings, fibers, threads, fabrics, packaging objects, such as, bottles and other containers and labels. Embodiments of the invention find particular application as security features that indicated whether a mechanical deformation has occurred. Some materials according to the present invention may also be used as adhesives. Thin films of blends of BCMDB and isotactic polypropylene (i-PP) were prepared by guest-diffusion, i.e., by swelling the i-PP films with solutions of the dye in $CHCl_3$ of different concentrations and at different temperatures. Most interestingly, as is apparent from FIG. 7, the PL spectra of the films thus obtained strongly depend on the diffusion conditions. Films that were dyed at low dye concentration, approximately 10 mg/mL, and at room temperature exhibit an emission that is characteristic for single molecules, with maxima at 492 and 526 nm, and a weak shoulder at 569 nm. By contrast, films that were dyed at a higher dye concentration, approximately 30 mg/mL, and at 60° C. feature an emission band that appears to be composed of a comparably small component associated with single molecule emission (with peaks at 492 and 530 nm), and a dominant component (with maximum at 644 nm) characteristic for the emission of aggregates. Thus, it appears that the extent of aggregation of the dyes in the polymer matrix and the intermolecular electronic interactions and photophysical characteristics of these blends, can indeed be conveniently controlled via the conditions applied to produce these materials.

This effect is consistent with strong $\pi$-$\pi$ overlap in the crystalline lattice of these molecules, which may be associated with the formation of excimers that are responsible for low-bandgap emission. We have shown that the emission characteristics of these dyes can be readily and conveniently manipulated by controlling their supramolecular structure. In particular the possibility to shift the emission of BCMDB by about 150 nm by simply changing the conditions under which blends of the dye and an inert host material are prepared.

The emission colour of a 'dyed' polymer can be readily tailored by controlling the extent of aggregation (and therewith the contribution to the PL spectrum of excimer vs. monomer emission) of a low-molecular cyano-OPV guest comprised in the polymer host. Literally any linear combination of monomer and excimer emission can be achieved, by changing the supramolecular structure of the polymer-dye mixture via its composition, the processing conditions, or the temperature.

Photoluminescent cyano-OPVs employed to exemplify further embodiments of the invention are BCMDB, BCEDB, BCMB, and 2,5-bis-(α-cyano-4-methoxystyryl)-thiophene ("BCMT"). BCMT was synthesized by the Knoevenagel reaction of (4-methoxyphenyl)acetonitrile with thiophenedicarboxaldehyde. The chemical structure of BCMT shown in Scheme 2:

The PL emission of all four dyes exhibits a pronounced bathochromic shift

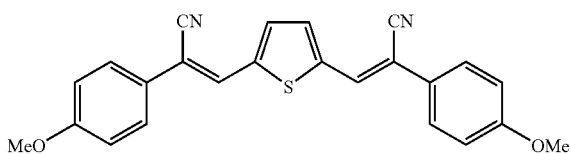

and significant broadening when comparing the crystalline solids with dilute solutions
(Table 1)

TABLE 1

| Dye | Abs. λmax solution[1] [nm] | PL λmax solution[1] [nm] | PL λmax crystalline solid[2] [nm] |
|---|---|---|---|
| BCMDB | 365, 436 | 506, 538 | 644 |
| BCMB | 389 | 461, 486 | 550 |
| BCMT | 439 | 505, 537 | 592 |
| BCEDB | 371, 440 | 508, 541 | 619 |

[1]Measured in $CHCL_3$ with a dye concentration of ca 2–2.5 $10^{-3}$ mol · $L^{-1}$.
[2]Semicrystalline powder as received from the synthesis.

With a shift of 106-138 nm, the effect is most pronounced in case of BCMDB. For these embodiments, linear low-density polyethylene ("LLDPE") was used as an example host material with two different ethylene/octene copolymers, which contained 1.2% (LLDPE-1.2-C8) and 9.3% (LLDPE-9.3-C8), respectively, of octene. These materials feature rather different density (0.942 and 0.919 g/cm$^3$) and solubility parameters, and as a result are swollen to different extents if immersed in a certain dyeing solution. Thin films of blends of the host polymer and the PL dyes were prepared by guest-diffusion, i.e., by swelling the LLDPE films with solutions of the dyes in $CHCl_3$ and toluene of different concentrations and at different temperatures. The variation of the dyeing parameters, such as concentration, temperature, and time, resulted in varying the amount of dye incorporated in the films.

Figure 8A:
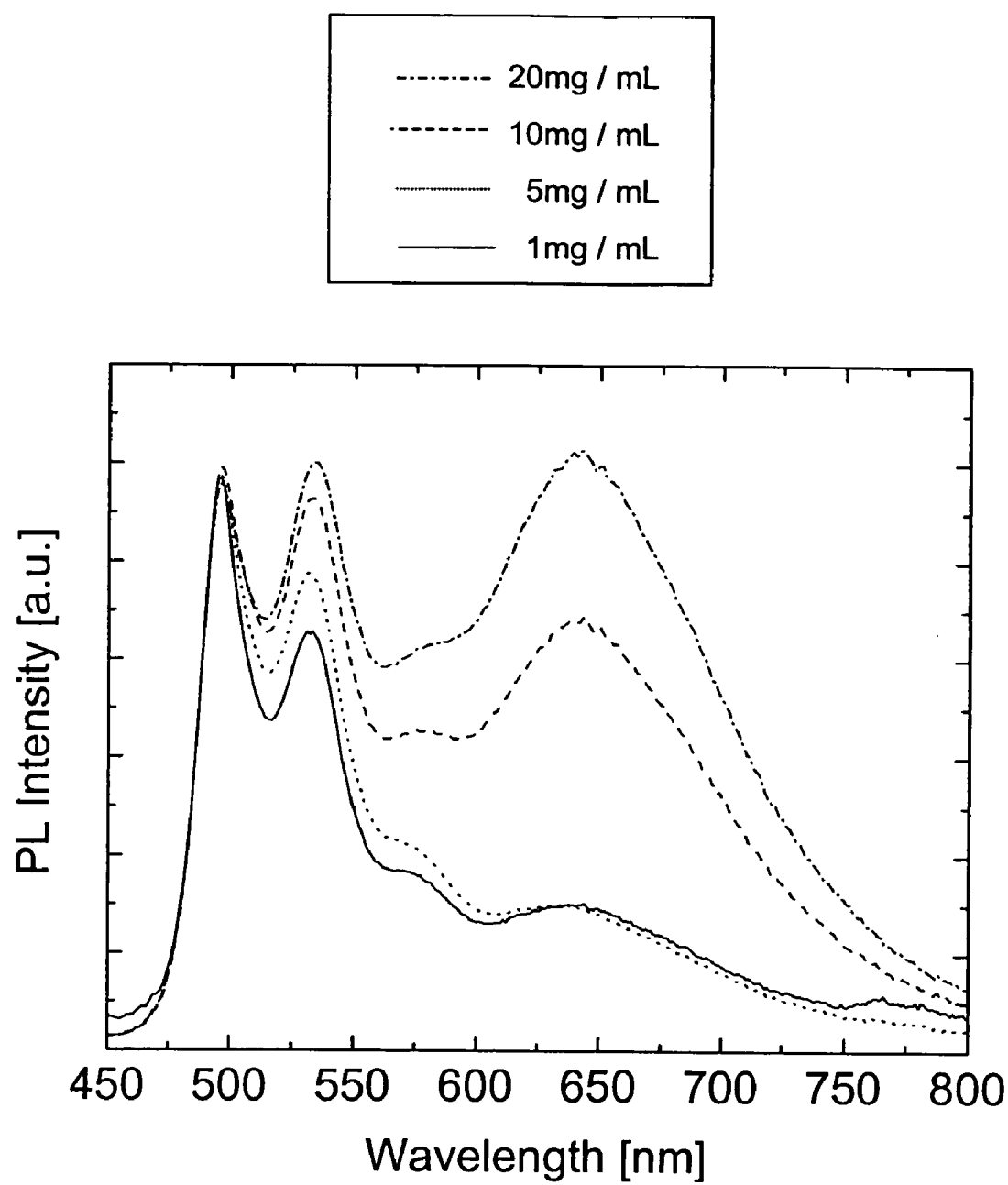
FIGS. 8A-8D are PL emission spectra of blend films LLDPE and BCMDB, LLDPEs containing 1.2% (FIGS. 8A and 8B) and 9.3% (FIGS. 8C and 8D) octene as a co-monomer were used, the samples were immersed for 16-18 h in $CHCl_3$ at 60° C.
Figure 8B:
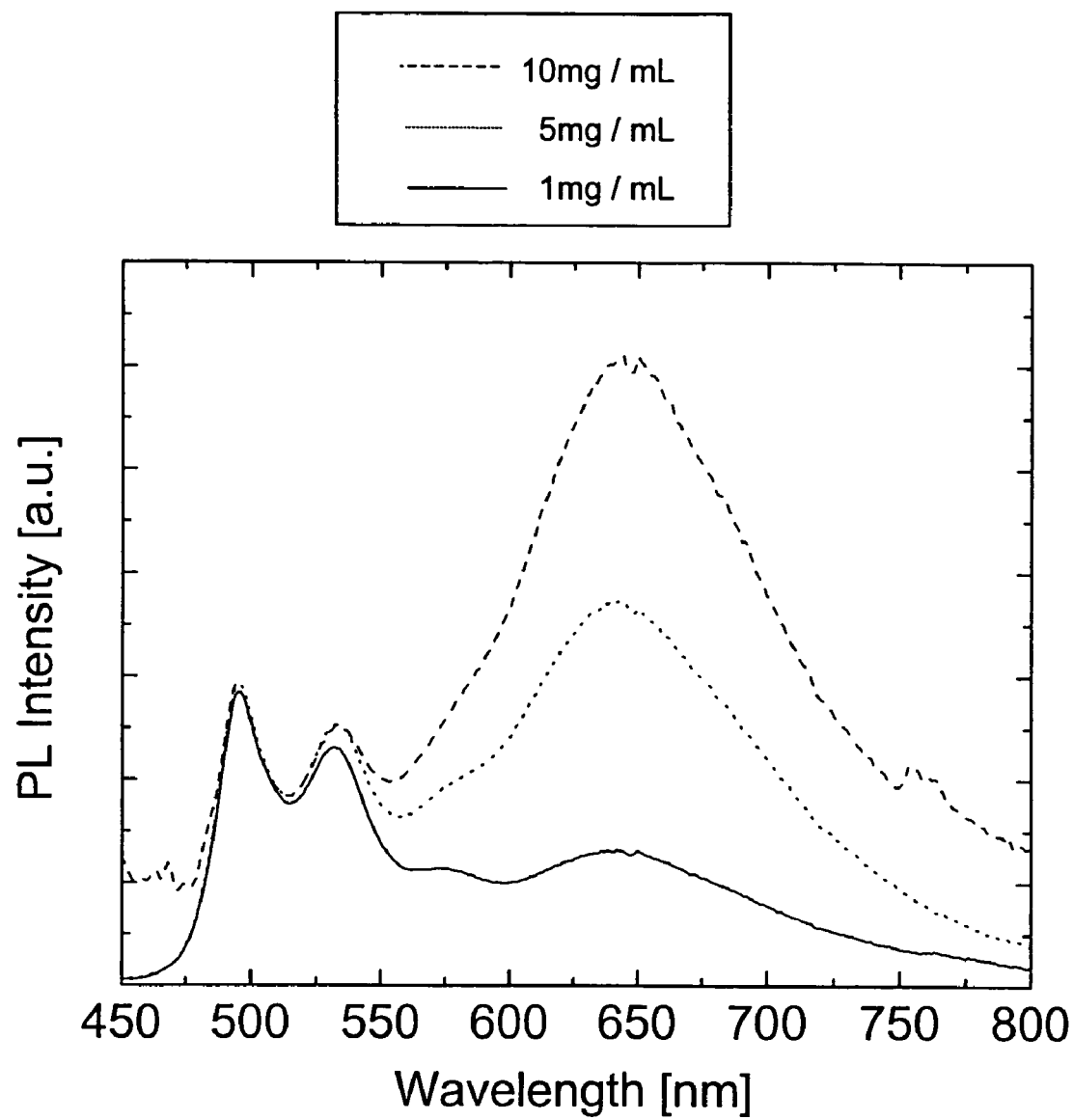
Figure 8C:
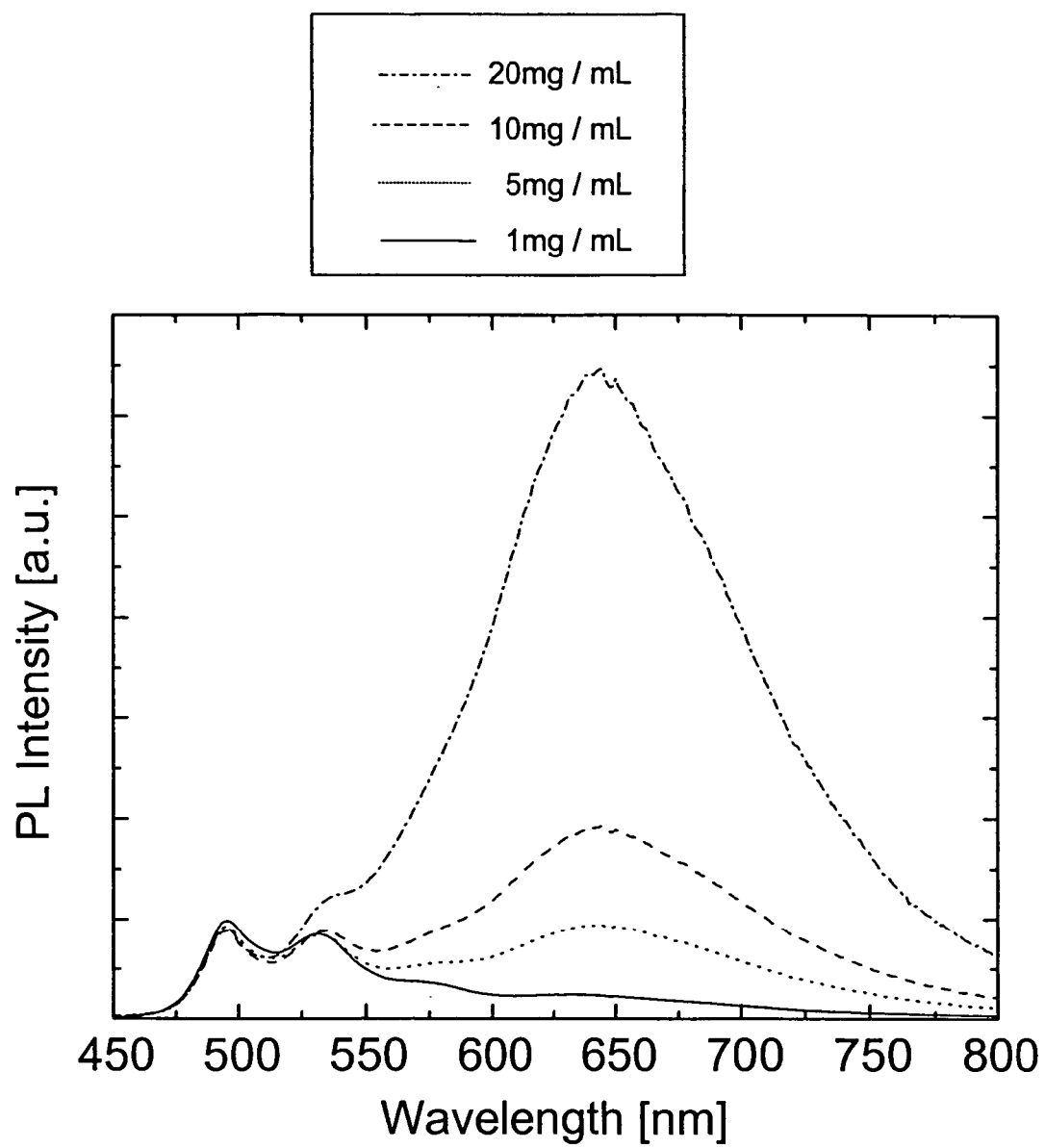
Figure 8D:
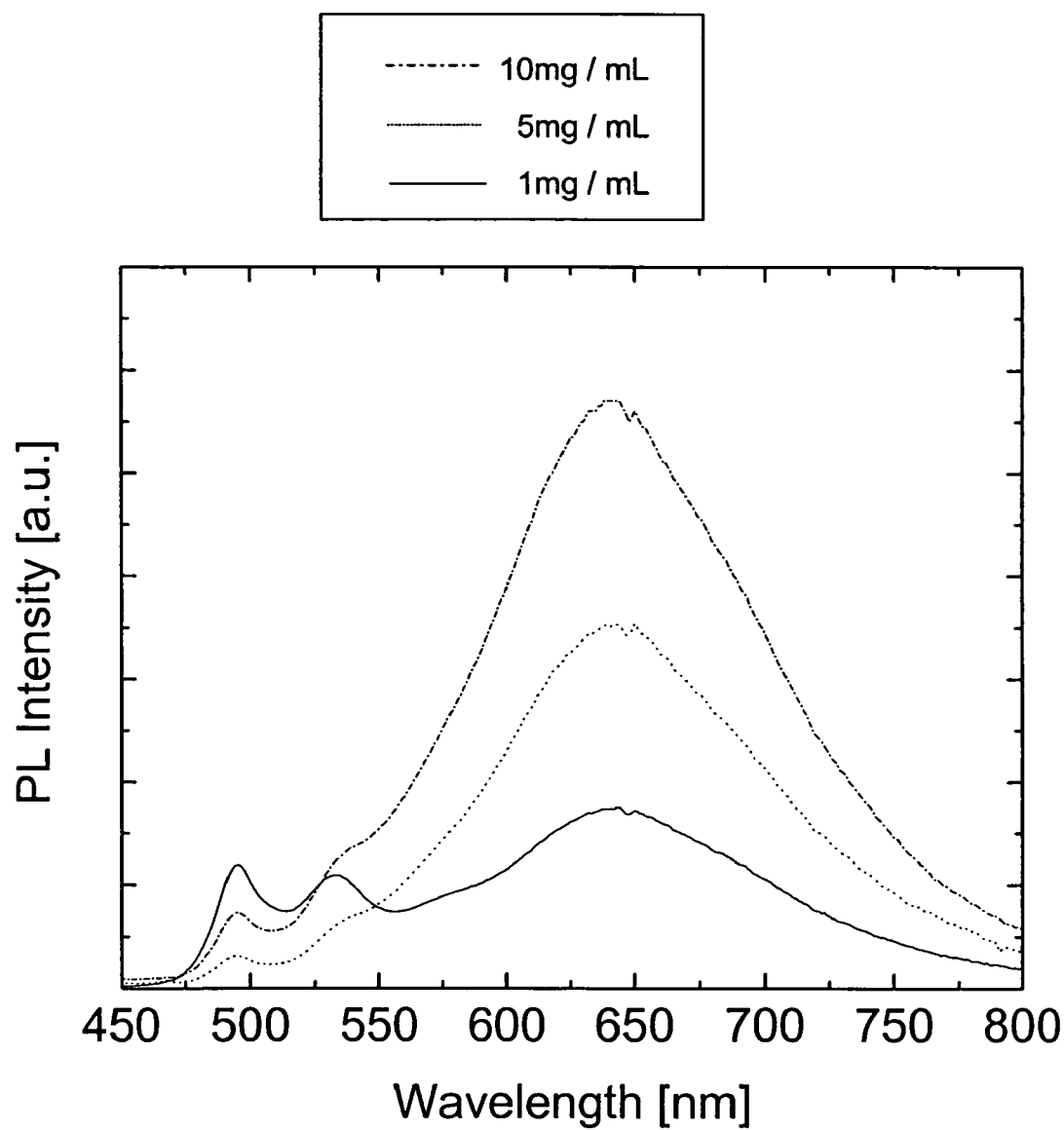

If dyed for a short period (~5 h) at room temperature in a low-concentration $CHCl_3$ solution of BCMDB (1 mg dye/mL solvent), films of both LLDPE grades fluoresce green and display emission spectra that feature well-resolved vibronic structures. The spectrum displays a modest (10 nm) hypsochromic shift when compared with the one of a $CHCl_3$ solution of the dye, but otherwise matches the monomer emission spectra well. Thus, the photophysical data suggest that under these dyeing conditions, the guest molecules are incorporated in the amorphous fraction of the semicrystalline host polymer in low concentration and in an apparently molecularly dispersed or dissolved fashion. The situation changes significantly if the concentration of the dye in the dyeing solution, the dyeing temperature, and the dyeing time are increased. FIG. 8A shows an example of a host material of LLDPE-1.2-C8 that was dyed with BCMDB, that in addition to the 'green' monomer emission with well-resolved peaks around 496 and 531 nm, the films develop a broad unstructured 'red' emission band around 644 nm. This band matches the one observed for the crystalline BCMDB and is indicative of excimer emission, which, of course, implies aggregation of multiple dye molecules. Keeping immersion time (16-18 h) and temperature (60° C.) constant, the relative intensity of the red band gradually increases with increasing dye concentration in the dyeing solution (FIG. 8A). The concentration of dyeing solutions was 1 mg/ML, 5 mg/ML, 10 mg/ML, and 20 mg/ML of BCMDB in $CHCl_3$. This finding is concomitant with a higher dye concentration in the film and an increased probability for aggregation and excimer formation. Indeed, UV-Vis absorption and PL excitation spectra (detection at 530 nm) confirm a higher optical density and show that the absorption spectrum of the films remains otherwise unchanged, which also points to excimer formation as the cause of the change in emission characteristics. FIG. 8B shows an example of the same dye/polymer combination, however, the dyeing temperature and solvent are charged the emission shift effect is more pronounced when increasing the temperature to 70° C. and exchanging $CHCl_3$ for toluene, which is a slightly better solvent for LLDPE. FIGS. 8C and 8D demonstrate that the effect is further amplified when using LLDPE-9.3-C8 instead of LLDPE-1.2-C8, consistent with the higher solubility of the dye in this polymer, which leads to an even further increased concentration of BCMDB in the dyed films. As can be seen from FIGS. 8C and 8D, the emission of highly dyed LLDPE-9.3-C8/1 blend films is predominantly governed by excimers, while monomer emission is of comparably low intensity.

Analogous experiments under similar conditions with dyes BCMB and BCMT, using $CHCl_3$ as the solvent were also conducted. If dyed for 16 h at room temperature in low-concentration solutions (1 mg dye/mL solvent), films of both LLDPE grades fluoresce blue for BCMB and green for BCMT, respectively, and display emission spectra that, except for a small hypsochromic shift, match well with the ones of $CHCl_3$ solutions of the dyes. Attempts to apply these dyes from more concentrated solutions were stifled by their limited solubility in $CHCl_3$ (~5 mg/mL at 60° C.) and also toluene. Other suitable solvents may be used. As a result, LLDPE-9.3-C8 films dyed in a saturated $CHCl_3$ solution of BCMB displayed an emission band that appeared to be related to excimer formation (centred at 551 nm). Although BCMT displayed a somewhat higher solubility in $CHCl_3$ than BCMB (~10 mg/mL at 60° C.), the emission spectra of LLDPE films dyed with this chromophore displayed only the characteristic features of monomer emission. This finding seems to indicate that the aggregation tendency of this thienylene vinylene dye in an LLDPE matrix is lower than that of the cyano-OPVs investigated here. We have also conducted experiments with 1,2-dichlorobenzene (DCB) as the solvent. A film based on LLDPE-1.2-C8, immersed (95° C., 16 h) in a DCB solution of BCMT (20 mg/ml) displayed a broad emission band with a maximum around approximately 600 nm, which appears to originate from excimer emission.

Effects of Mechanical Deformation and Aging

Figure 9A:
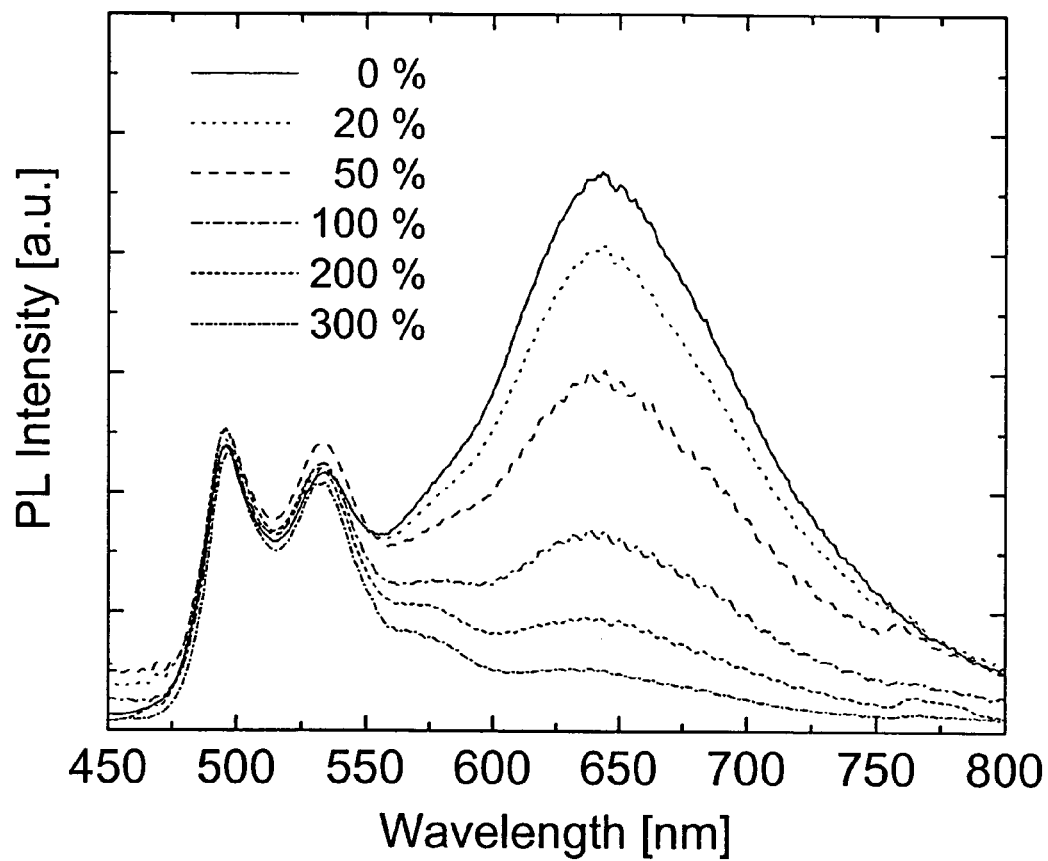
Figure 9B:
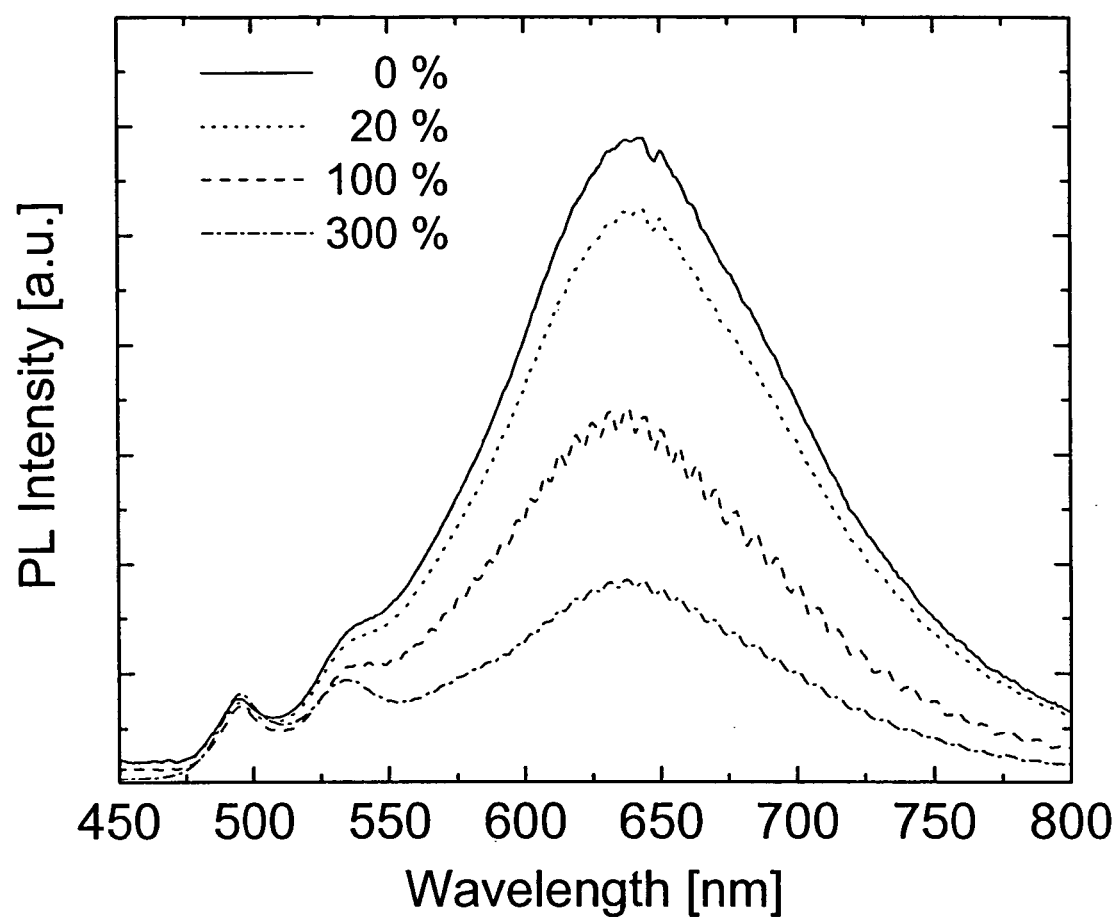

The influence of solid-state tensile deformation on the emission characteristics of blends of BCMDB and LLDPE was also investigated. FIGS. 9A-9B show the PL spectra of films of LLDPE-1.2-C8 and LLDPE-9.3-C8, respectively, which were dyed with a solution of BCMDB (~10 mg/mL at 70° C.) in toluene, and drawn at room temperature to draw ratios, $\lambda=(I-I_o)/I_o$, of up to 400%. Most interestingly, in both systems the relative intensity of the 'red' excimer band is substantially reduced upon drawing. In case of the LLDPE-9.3-C8 blend film (FIG. 9B), the emission spectrum remains dominated by the broad low-energy band. By contrast in FIG. 9A, the LLDPE1.2-C8 blend film undergoes a most striking transformation and the emission spectrum changes from an excimer-dominated band to an almost pure green, at a draw ratio of only 200-300%. Tensile deformation can indeed cause the transformation of a phase-separated polymer blend into an apparent molecular dispersion or solution.

Figure 9C:
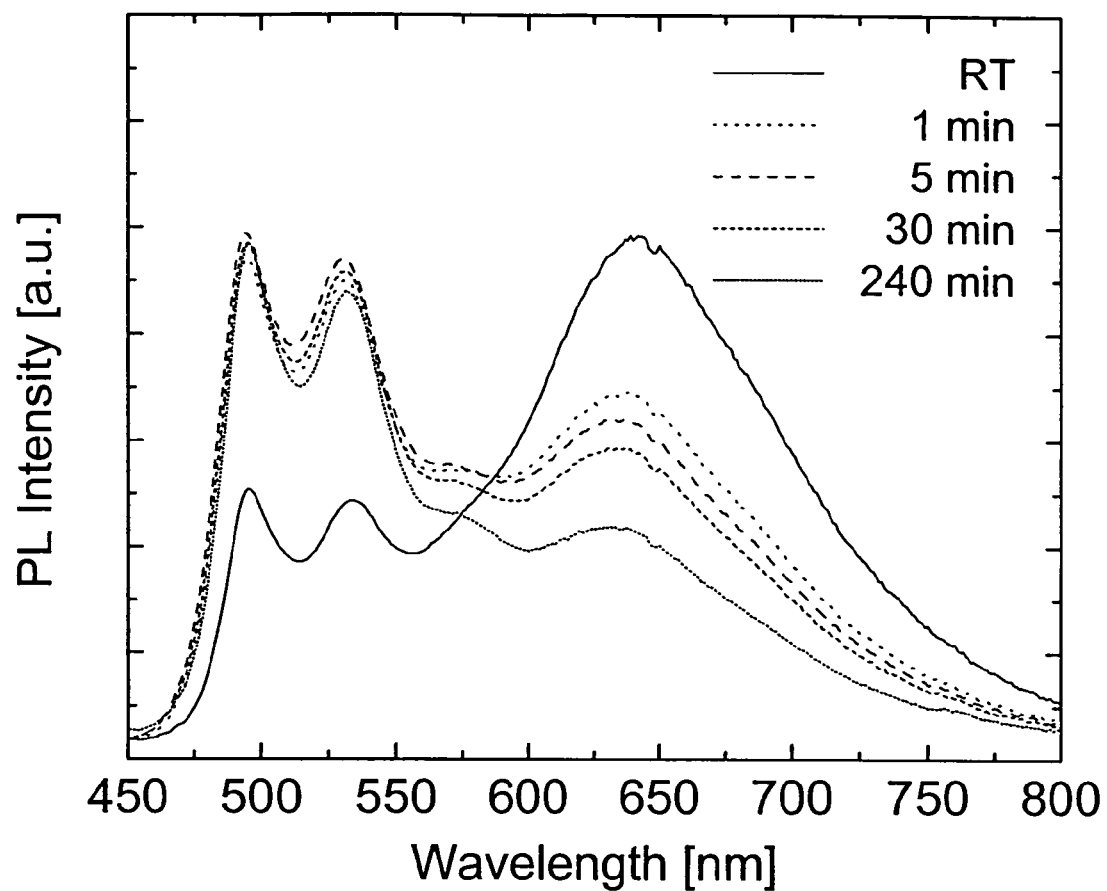

FIG. 9C shows the influence of temperature on the emission characteristics of the blends of the present invention. While the emission spectra remained essentially unchanged when at annealing or aging the films at temperatures below 65° C., the relative intensity of the 'red' excimer band was substantially reduced when annealing the films at higher temperatures, as shown for an LLDPE-1.2-C8 based blend in FIG. 9C. As is evident from the graph of FIG. 9C, the process is relatively slow at 85° C. and a substantial excimer emission remains present after annealing for a few hours. Interestingly, the transition to an almost pure green emission was accomplished in approximately 5 min, if the annealing temperature was increased to 95° C. Thus, the segregation of the aggregated dye molecules can also be thermally stimulated. The pronounced temperature sensitivity in a regime that overlaps with the melting range of the host material suggests that this effect is directly connected to the mobility of the host molecules.

Figure 10A:
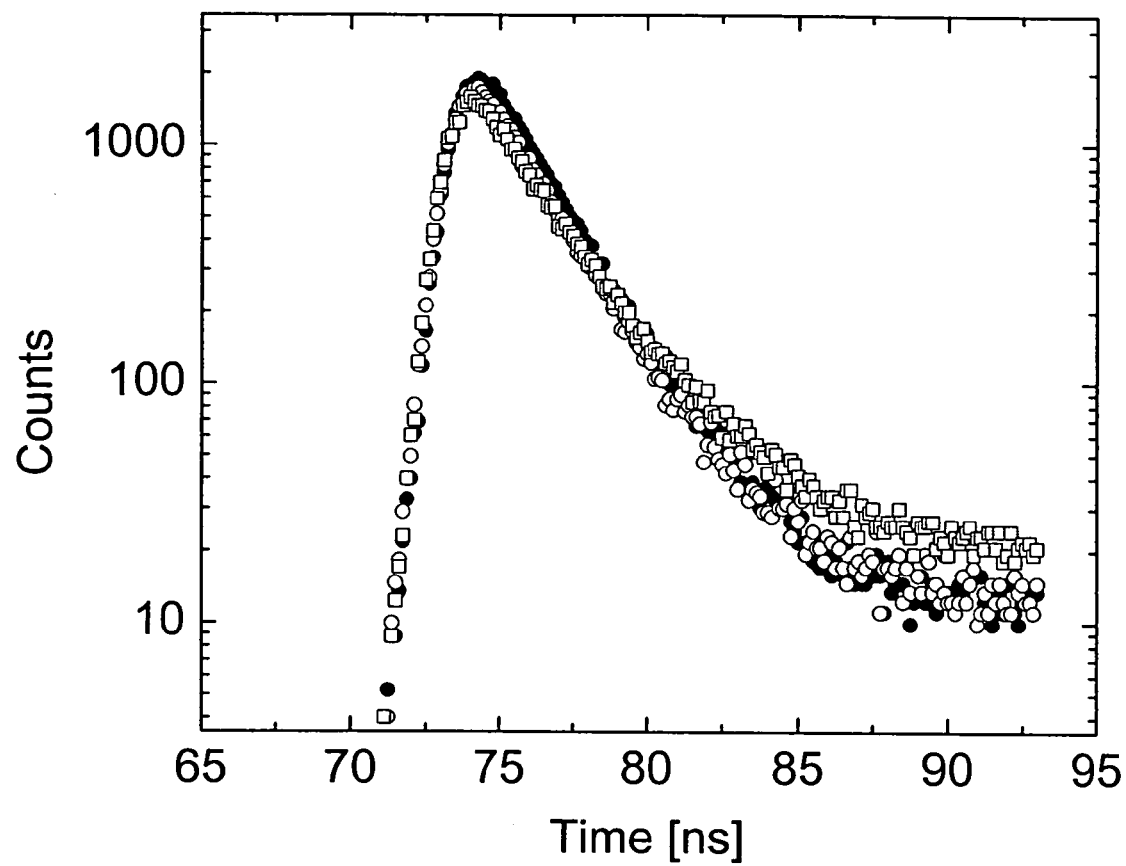
FIGS. 10A and 10B are the PL decay curves of blend films of LLDPE-1.2-C8 and BCMDB measured under excitation at 481 nm at 530 (FIG. 10A) and 650 (FIGS. 10B) nm, wherein the films were dyed in $CHCl_3$ at 65° C. using dye concentrations of 5 (•) and 30 mg/mL (o), the film of FIG. 10B was also measured after being stretched at room temperature to $\lambda$=200% (□).
Figure 10B:
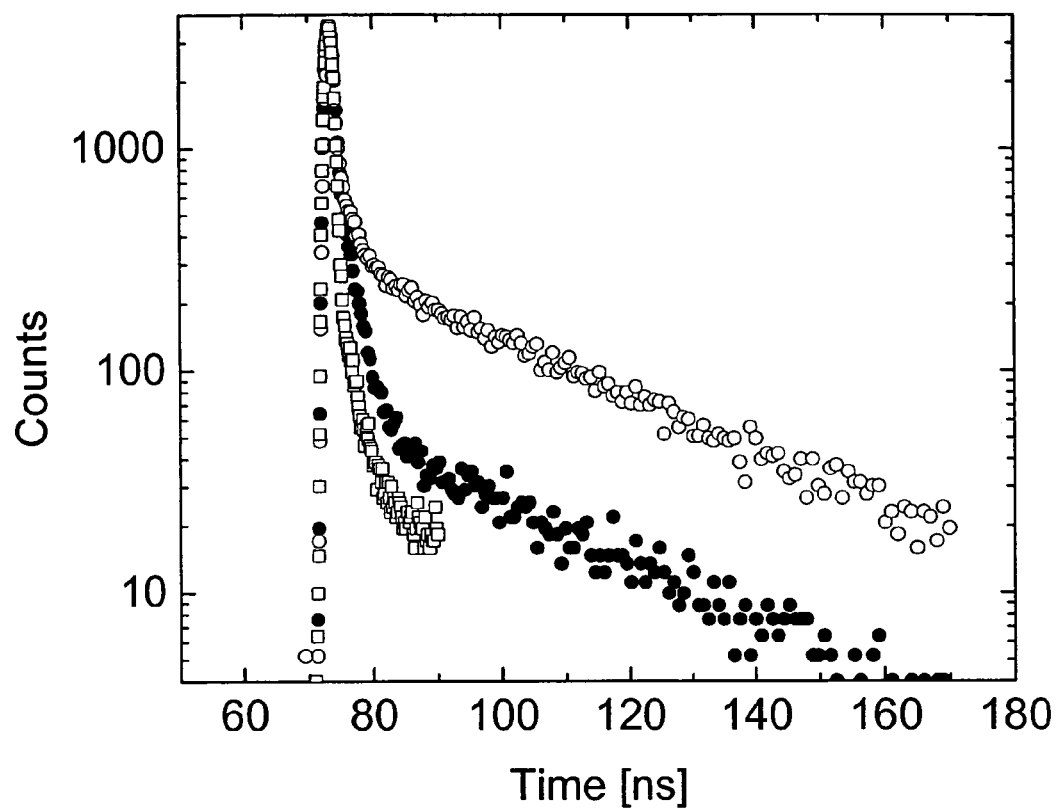

In order to provide evidence of excimer formation and confirm the postulated molecular architectures of the materials investigated, we have conducted PL lifetime measurements on LLDPE-1.2-C8 blend films dyed in CHCl$_3$ at 65° C. using dye concentrations of 5 and 30 mg/mL were generated. The steady-state PL spectra of these films follow the trends depicted in FIG. 10A, and are dominated by monomer (low-concentration sample) and excimer (high-concentration sample) emission, respectively. The PL decay curves of these films, measured at 530 and 650 nm are shown in FIGS. 10A and 10B, together with the data of the high-concentration sample, collected after stretching the film at room temperature to $\lambda$=200% in FIG. 10B. The PL decay curves to show double-exponential dependencies, with lifetimes of about 2 and 20 ns, which are typical values for the monomer and excimer emission of small organic dyes, respectively. The contribution of the fast decay dominates the measurements conducted at 530 nm (FIG. 10A), while the long-lived excited states contribute predominantly to the decay curves recorded at 650 nm (FIG. 10B). The contribution of the long-lived excited states is only substantial in case of the high-concentration sample, while the decay behaviour of the low-concentration sample as well as the stretched film are dominated by monomer decay.

The emission color of blends of a host polymer and a low-molecular cyano-OPV can readily be manipulated over a wide range by controlling the extent of aggregation of the photoluminescent dye. Data from the embodiments document that the cyano-OPV BCMDB is particularly attractive for this purpose, since the colors of monomer (green) and excimer (orange-red) emission span an unusually large range, and virtually any linear combination of green and red PL emission, is accessible. The supramolecular structure, and therewith the emission colour, of LLDPE/dye blends as well as other host material/dye blends, is readily tuned via the composition, the processing conditions, or the temperature.

Conventional Polymer Melt Processing

Embodiments of the present invention also include materials prepared by conventional melt-processing techniques, if the phase behavior is adequately controlled.

Binary blends of LLDPE (4.00 g) and BCMDB (7.2, 8.0 and 16.0 mg, i.e., 0.18, 0.20 and 0.40% w/w) were prepared by feeding the components into a recycling, corotating twin-screw mini-extruder (DACA Instruments, Santa Barbara, Calif.), mixing for 5 min at 180° C., and subsequent extrusion. Blends comprising 0.01-0.15 wt % of BCMDB were prepared by diluting the above blends with neat LLDPE by melt mixing the components in the same manner. Films were prepared by compression-molding the blends between two aluminum foils and using four 110 μm spacers in a Carver press at 180° C. for approximately 3 min and immediately quenching the samples after removal from the hot press by immersion in an ice-water bath. The resulting blend films had a thickness of approximately 100 μm.

Steady-state PL spectra were acquired on free-standing films on a SPEX Fluorolog FL3-12. All spectra for these films were collected under excitation at 435 nm and corrected for the instrument throughput and the detector response. PL spectra of films referred to as 'freshly prepared' were obtained within 4 hours of quenching.

Figure 11:
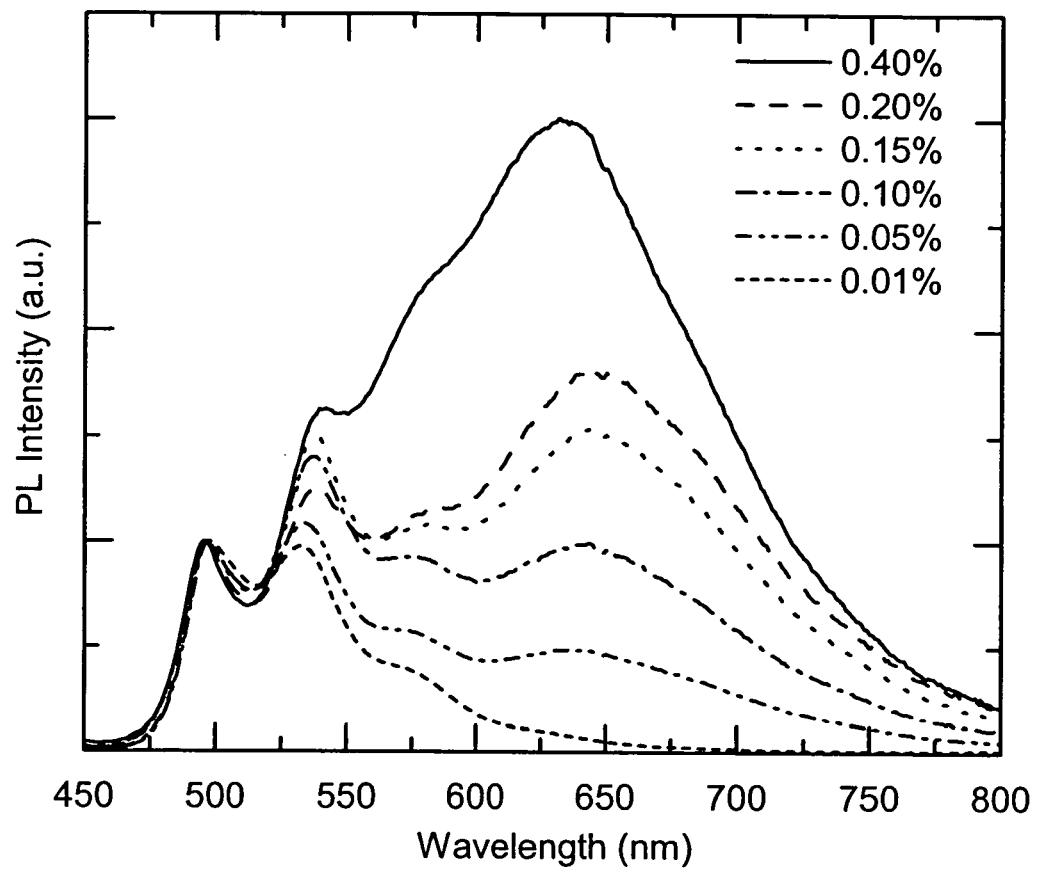
FIG. 11 is a graph of the photoluminescent intensity curve of freshly prepared LLDPE/BCMDB blend films as a function of dye concentration.

Films based on binary blends of LLDPE and between 0.01 and 0.40% w/w BCMDB were prepared by melt-mixing these two components in a co-rotating mini-extruder and subsequent compression molding as described above. The processing temperature of 180° C. was well below the melting temperature of BCMDB (248° C.). The films were rapidly quenched after melt pressing. Freshly prepared blend films comprising 0.01% BCMDB exhibited 'green' fluorescence and displayed an emission spectrum that featured well-resolved vibronic structures and is similar to the one of a molecular solution. See FIG. 11. Thus, the data suggest that the dye molecules are incorporated in the amorphous fraction of the LLDPE in an apparently molecularly dispersed or dissolved fashion. The situation changes significantly if the concentration of dye is increased. FIG. 11 shows that the freshly prepared blends develop a broad, unstructured 'red' emission band centered around 640 nm that increases with increasing dye concentration. This finding is concomitant with the higher dye concentration in the film, which leads to an increased probability for aggregation and excimer formation.

Figure 12:
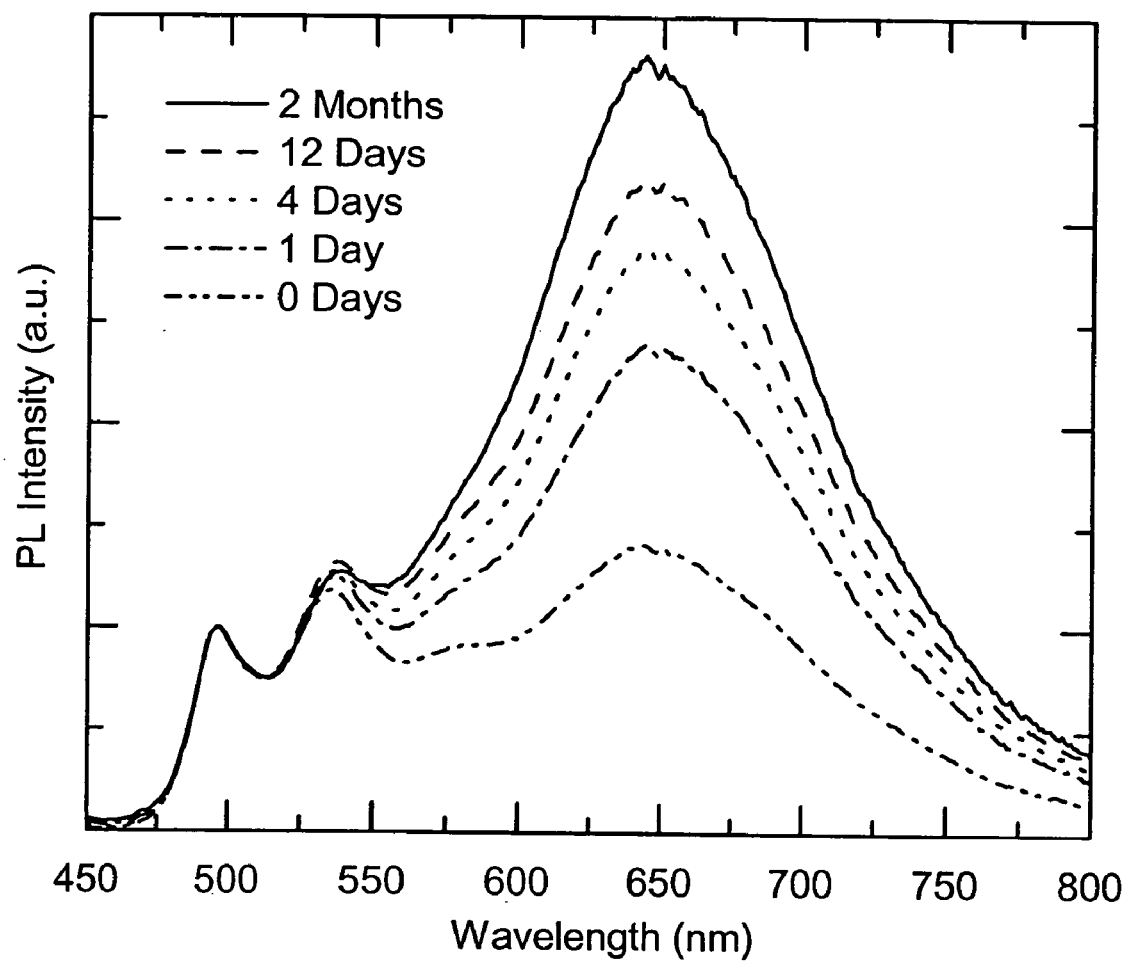
FIG. 12 is a graph of the photoluminescent intensity curves of LLDPE and 0.18 wt % BCMDB as a function of storage time under ambient conditions indicating the effect of aging.

Interestingly, in the case of films comprising 0.05 wt % BCMDB or more the intensity of the 'red' emission band around 640 nm increased upon storage under ambient conditions, as shown in FIG. 12 for a 0.18% w/w blend film. As can be seen from the figure, the rate of this process decreases sharply as a function of time and appears to approach zero after a timeframe of a few months. This behavior seems to be a direct consequence of the quenching step and reflects the changing phase behavior of the system upon cooling and storage. It appears that during melt processing most, if not all, of the dye is dispersed in the molten polyethylene, at least in case of the rather dilute compositions investigated here. This interpretation is consistent with the fact that if heated to 180° C., all blends displayed virtually exclusively the 'green' emission band characteristic of molecular emission. Rapid quenching allows to kinetically 'trap' the system such that a substantial fraction of the dye molecules remains molecularly dispersed in the LLDPE. However, the resulting blends seem to be thermodynamically unstable under ambient conditions, leading to slow de-mixing and aggregation of the dye molecules.

Figures 13A, 13B, 13C:
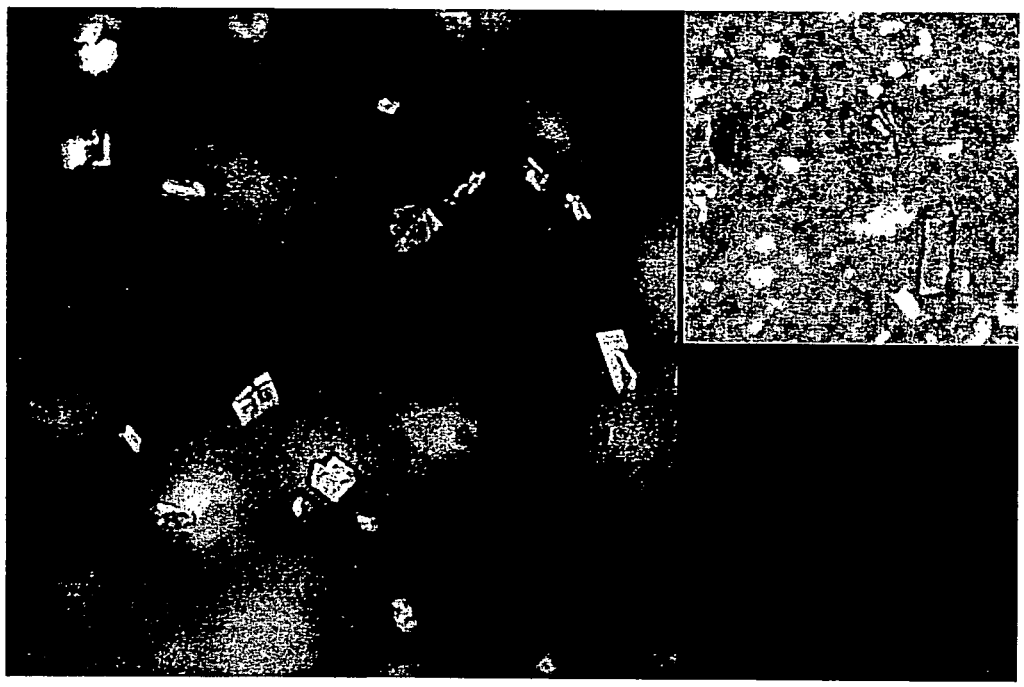
FIGS. 13A-13C are cross polarized optical micrographs depicting the cooling process of a blend of LLDPE and 0.40 wt % BCMDB at 180° C.

The cooling of molten LLDPE/BCMDB mixtures by means of polarized optical microscopy. As shown in FIGS. 13A-13C for a blend comprising 0.40% w/w of BCMDB, at 180° C. the refraction of light in anisotropic materials (as calcite) in two slightly different directions to form rays all blends form non-birefringent homogenous melts. This finding is initially surprising (but most desirable from an application point of view), since the melting temperature of the dye is well above the processing temperature. It appears that molten LLDPE is indeed a suitable solvent for BCMDB. Cooling the samples at rates (typically 5-10°/min) that were slow compared to the quenching procedure applied for the previous films, phase separation was observed, at least for blends comprising 0.20% w/w BCMDB or more. The optical micrographs unequivocally show that the dye crystallized at temperatures above the crystallization temperature of the LLDPE matrix. The extent of phase separation (and there with the materials optical properties) not only depends on the blend's composition, but can also be controlled via the processing conditions.

Figure 14:
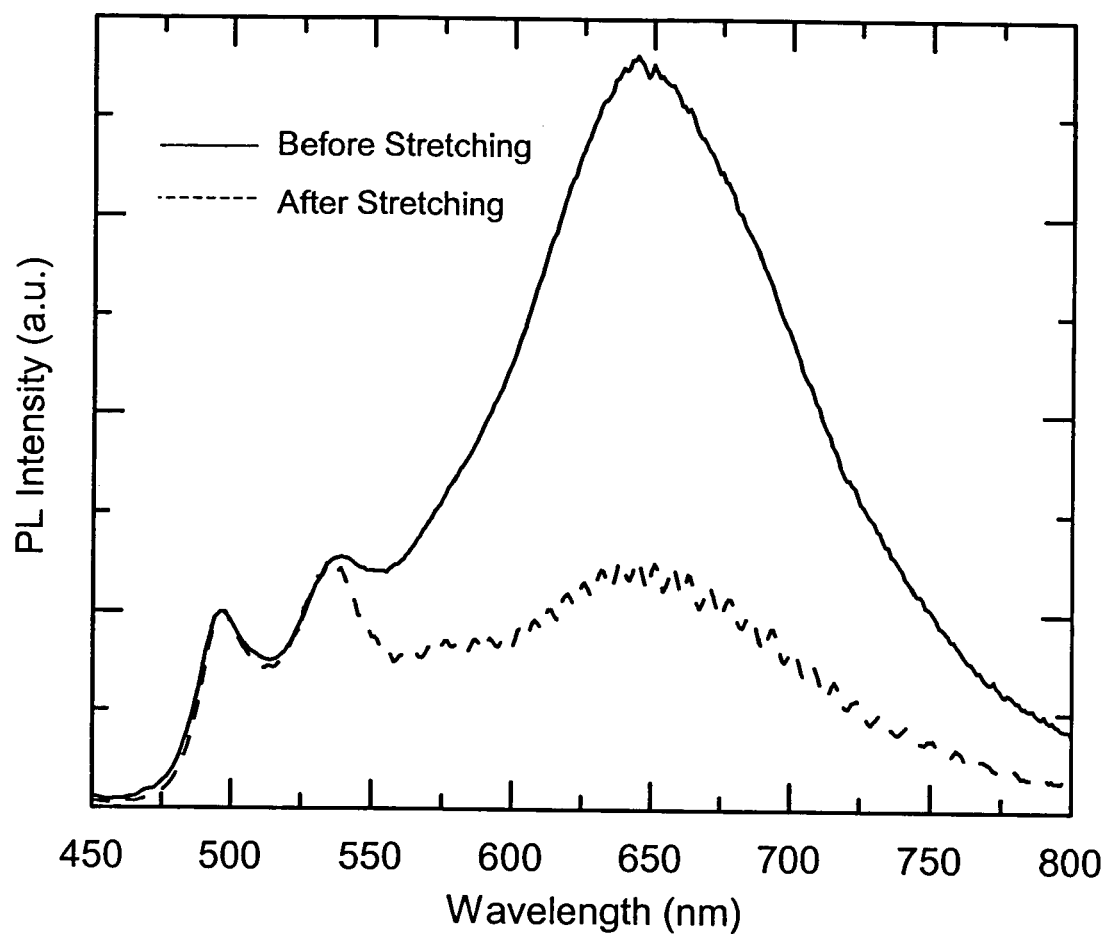
FIG. 14 is a graph of the photoluminescent intensity curves of a blend of LLDPE and 0.18 wt % BCMDB before and after mechanical deformation by stretching.

FIG. 14 shows the PL spectra of an (aged) blend film of LLDPE and 0.18% w/w BCMDB before and after stretching the film at room temperature to a draw ration $\lambda=(I-I_o)/I_o$ of 500%. Gratifyingly, the relative intensity of the 'red' excimer band is substantially reduced upon drawing. Tensile deformation can indeed cause the transformation of a phase-separated polymer blend into an apparent molecular dispersion or solution. Interestingly, for a given composition (e.g., 0.18% w/w BCMDB) the emission spectrum of the stretched portion of the blend films was found to be the same, irrespective of whether or not the film was aged before stretching. Also, it should be noted that the emission spectra of the drawn films were stable with time, at least over a period of two months, which is concomitant with a considerably reduced mobility.

Binary blends of LLDPE and BCMDB can readily be produced via conventional melt processing techniques. Phase behavior of these materials can be minutely controlled via the blend's composition as well as the detailed processing conditions. While homogenous blends display the 'green' emission spectrum that is characteristic of the dye's monomer emission, de-mixing leads the formation of 'red'-light-emitting excimers. Virtually any linear combination of monomer mechanical deformation can cause substantial changes of the emission characteristics of such blends.

Solubility Effects

Binary blends of LLDPE (4.00 g) and BCMDB or BCMB (7.2, 8.0, and 16.0 mg, i.e., 0.18, 0.20, and 0.40 wt %) were prepared by feeding the components into a recycling, co-rotating twin-screw mini-extruder (DACA Instruments, Santa Barbara, Calif.), mixing for 5 min at 180° C., and subsequent extrusion. Blends comprising 0.02 and 0.05 wt % of BCMDB were prepared by diluting the above blends with neat LLDPE by melt mixing the components in the same manner. Blends comprising 0.40 and 1.0% w/w BCEDB were prepared in an aluminum dish on a hot stage between 170 and 180° C. by manually mixing 500 mg of LLDPE with 2 and 5 mg respectively of BCEDB for 10 minutes. Films were prepared by compression-molding the blends between two aluminum foils and using four 110 μm spacers in a Carver press at 180° C. for approximately 3 min and immediately quenching the samples after removal from the hot press by immersion in an ice-water bath. The resulting blend films had a thickness of approximately 100 μm.

Figure 15:
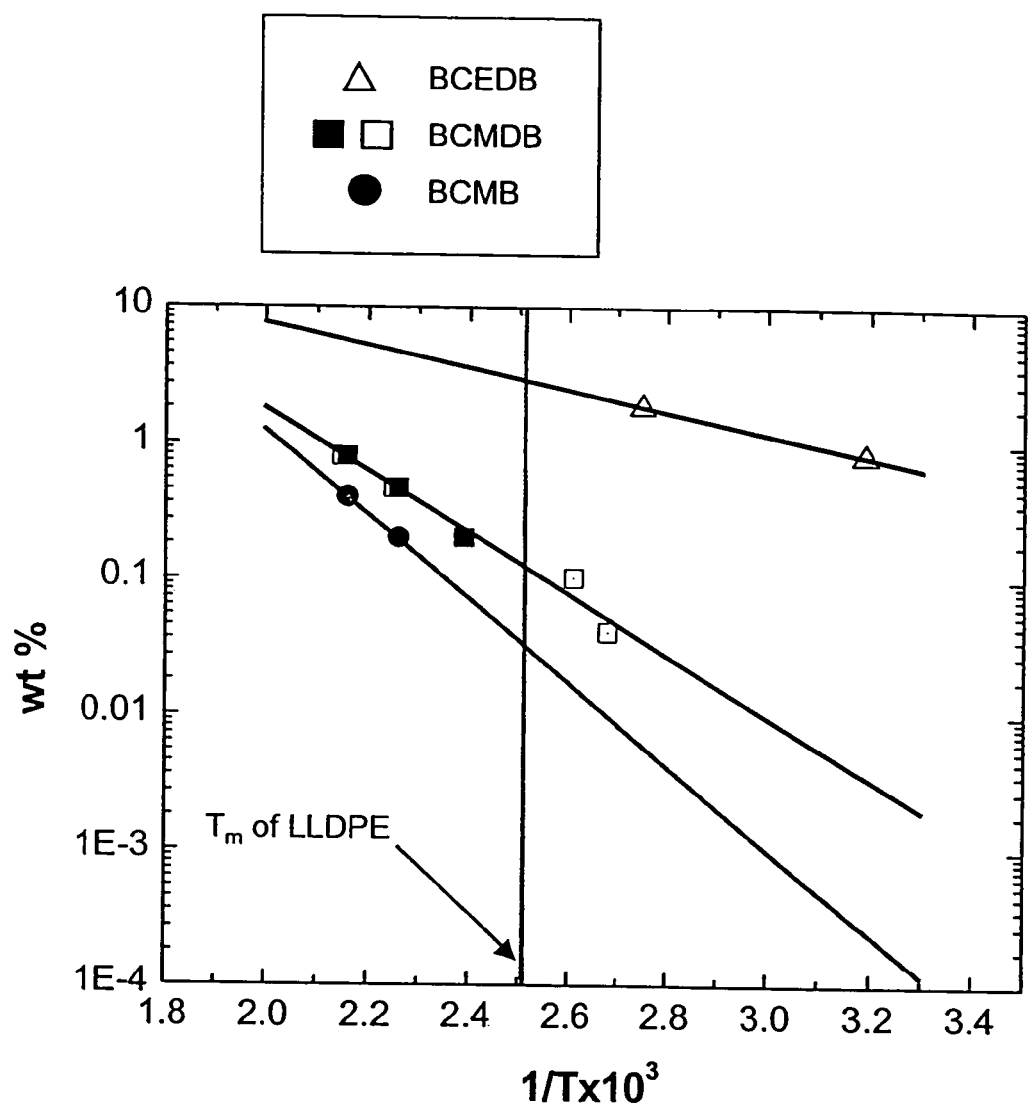
FIG. 15 is a graph of the solubility of BCEDB (Δ), BCMDB (■, □), and BCMB (•), wherein the filled symbols represent data obtained by PL spectroscopy and the empty symbols represent data obtained by polarized optical spectroscopy, at temperatures below the melting point of LLDPE, concentrations were corrected for a crystallinity of 51%.

The solubility of the OPVs in LLDPE was investigated in the temperature is regime between 20 and 180° C. using polarized optical microscopy and PL spectroscopy. See FIG. 15. The phase behavior of blends with a dye content of >0.20% w/w was characterized by optical microscopy. The temperature of the blends was increased in increments of 10° C. and the temperature at which the dye crystals (which had previously phase-separated from the LLDPE matrix) had completely dissolved was taken as the solubility limit. The phase behavior of blends of lower concentration was difficult to study by optical microscopy, since the crystals were either too small, or they dissolved below the melting temperature of LLDPE and light scattering from the LLDPE matrix impeded the microscopy. Thus, in this case PL spectroscopy was employed, and the solubility limit was defined as the temperature at which the characteristic signal of the excimer band had fully disappeared. Gratifyingly, these complementary methods provided consistent data and logarithmic plots of the solubility of the various dyes (in wt %) against 1/T display a linear relation, which is consistent with standard solution theory. As can be seen from FIG. 15, the absolute solubility of the dyes significantly varies with the molecular structure and sharply increases with the number and length of aliphatic substituents, which allow for favourable van der Waals interactions with the matrix. The comparison of the three different OPVs (BCMB, BCMDB, and BCEDB) indicates further that the temperature dependence of the solubility becomes less pronounced as the molar heat of the fusion of the dye decreases (109, 101, and 54 J/g). This finding appears to be consistent with a comparably weak temperature dependence of the Flory-Huggins parameter $\chi$. Thus, these results seem to suggest that the phase behavior of OPV/polyolefin blends can readily be controlled via (minor) chemical modifications of the molecular structure of the dye. Alternatively, it is believed that chemical modifications to the molecular structure of the polymer will also control the phase behavior of the blend.

Figure 16A:
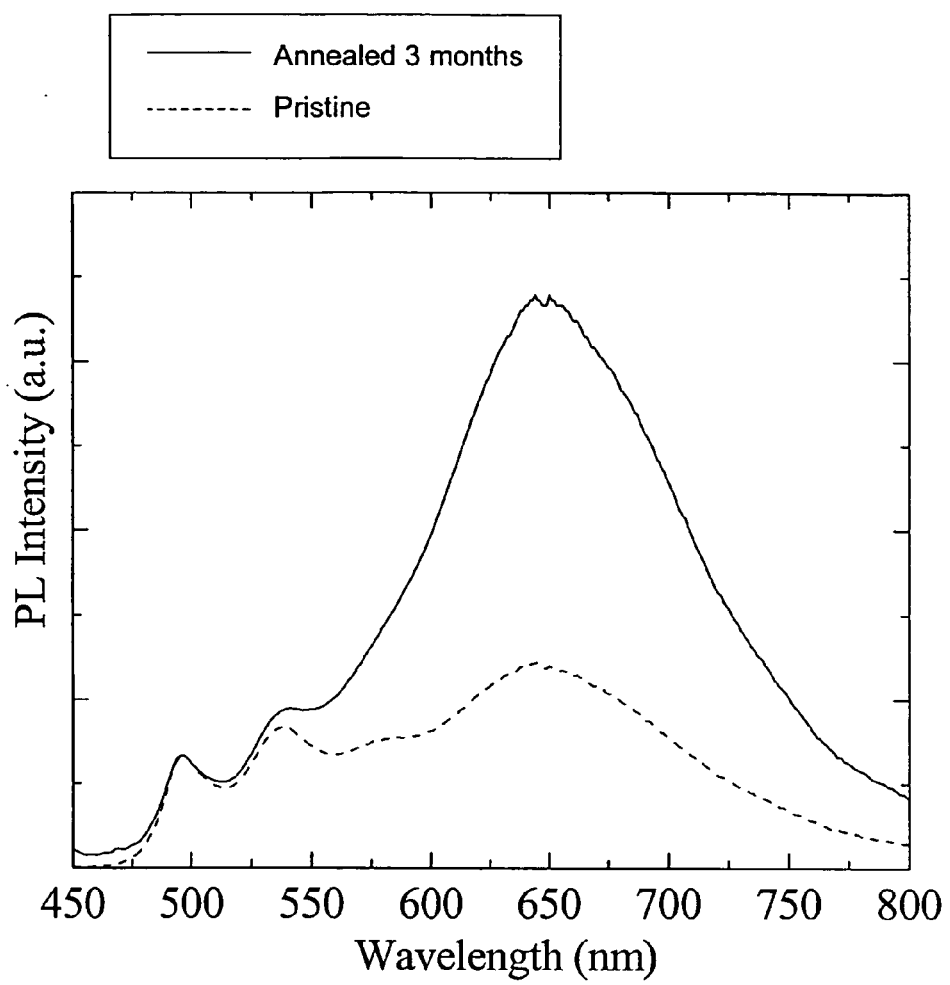
FIG. 16A is a graph of the PL spectra of blend films of LLDPE and ~0.18 wt % BCMDB freshly prepared (dotted lines) and aged (solid lines) for 3 months under ambient conditions (left)
Figure 16B:
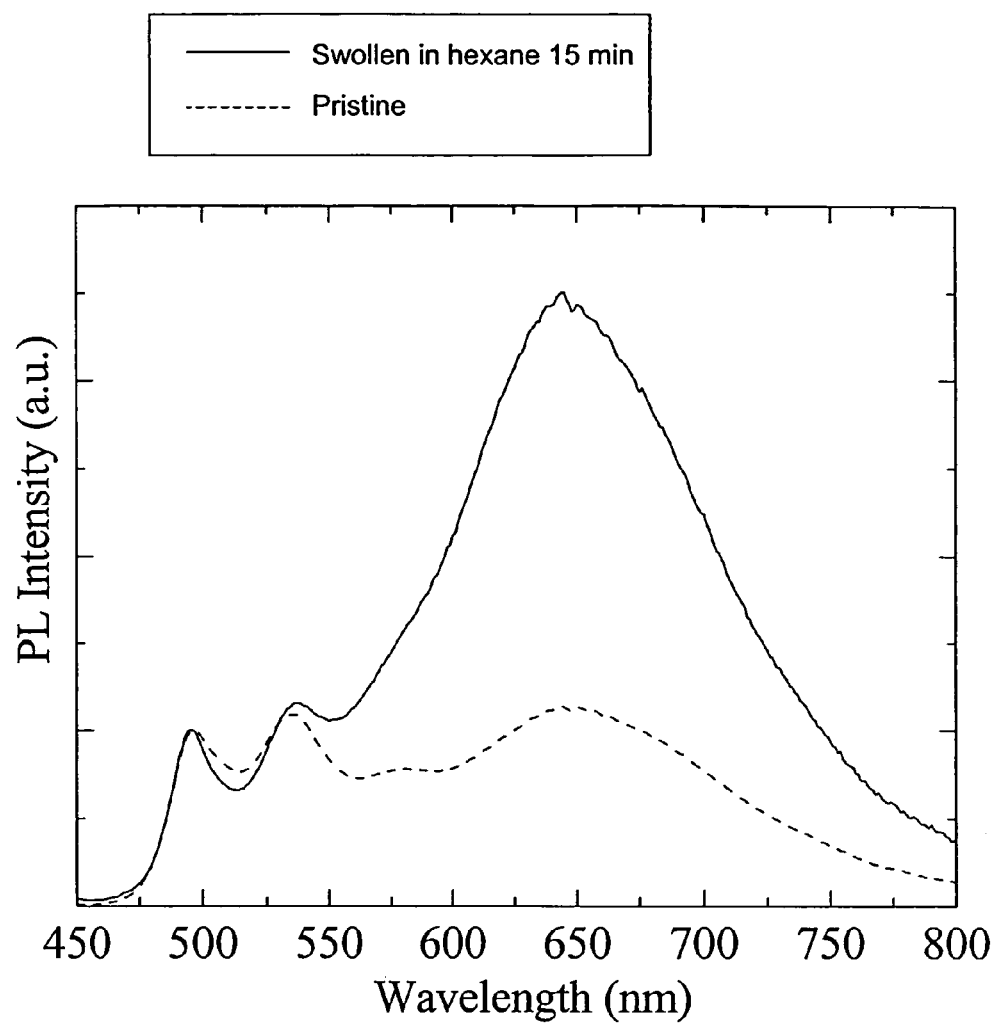
FIG. 16B is a graph of the PL spectra of the same blend swollen for 15 min in hexane (right)
Figure 17A:
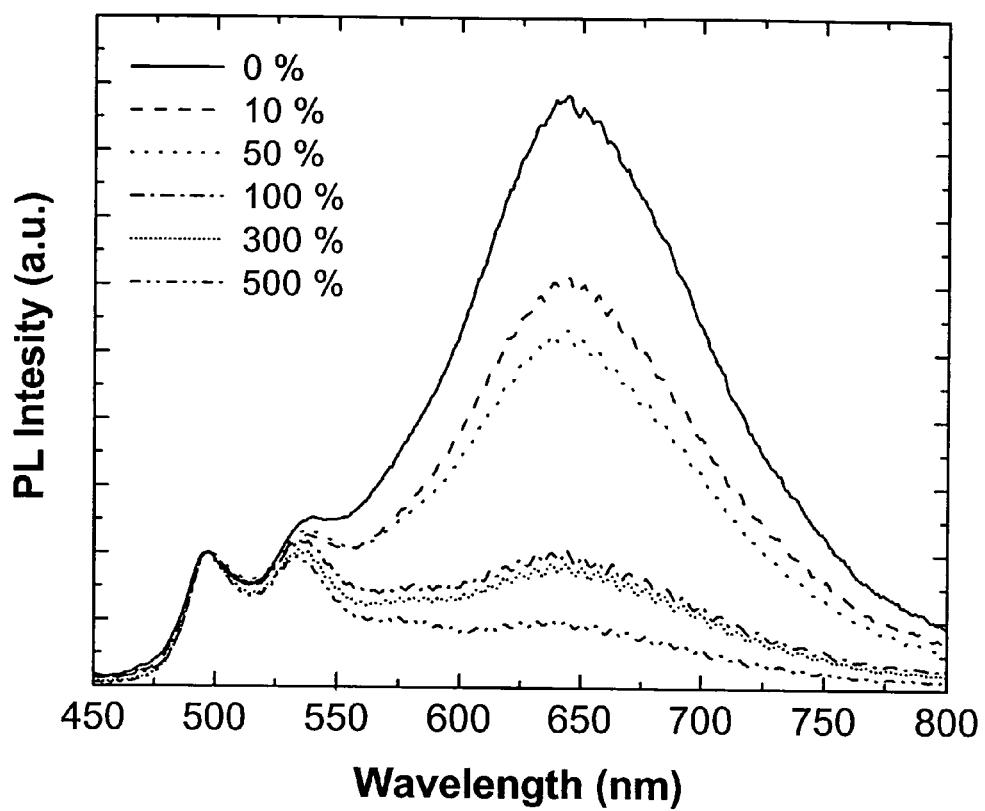
FIGS. 17A-17B are graphs of the photoluminescent intensity of blends of LLDPE and 0.20% w/w BCMDB (FIG. 17A) and 0.20% w/w BCMB (FIG. 17B) before and after stretching to different draw ratios $\lambda$.
Figure 17B:
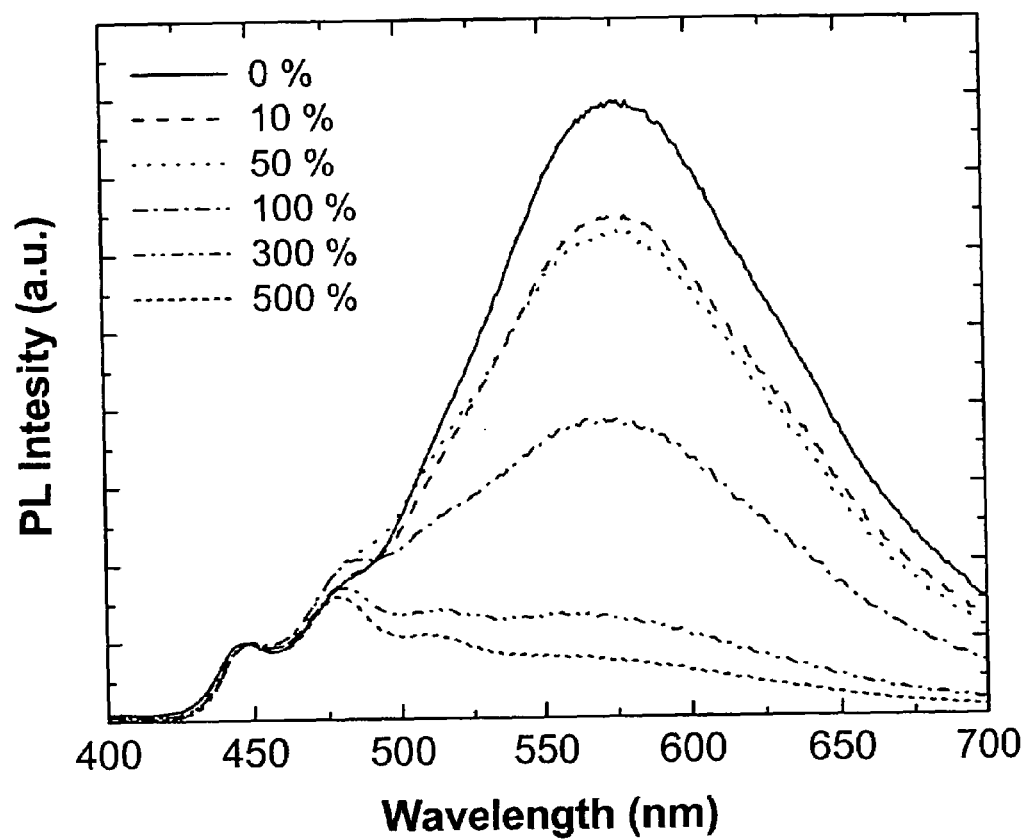

Phase-separated blends with apparently very small BCMDB aggregates can be produced by rapidly quenching the samples after melt-processing. Small dye aggregates may be important, if the dye molecules are to be used as integral strain sensors, since large-scale phase separation may prevent an efficient break-up of the excimers. However, in quenched blends the relative intensity of the excimer emission band is initially small, and only slowly increases upon storage under ambient conditions. This effect is attributed to slow de-mixing and aggregation of the dye molecules after being kinetically trapped upon rapidly cooling the blends to RT. In order to increase the speed of the de-mixing process, blend films were briefly swollen in hexane, which is a poor solvent for the OPVs but swells LLDPE well. Gratifyingly, due to the plasticizing effect of the hexane, the BCMDB molecules aggregated rapidly and the PL spectra of the films changed quickly upon immersion in hexanes. No significant change in PL spectra was observed after treatment for 15 minutes, and a comparison of the PL spectra of BCMDB (0.18%)/LLDPE blend films stored at ambient for three months and plasticized with hexane show similar results. See FIG. 16.

Solid-state tensile deformation has a pronounced effect on the emission characteristics of blends of LLDPE and BCMDB or BCMB. Upon stretching the films to a draw ratio $\lambda=500\%$, films of both materials (at dye concentration of approximately 0.2% w/w) display good visual contrast.

Concomitantly, PL emission spectra show a large reduction in the relative intensity of the excimer band. See FIG. 7.

Experimental

Methods: All chemicals were of highest commercial quality and were used as received. 2,5-Dimethoxy terephthaldicarboxyaldehyde was purchased from Ryan Scientific Inc., Isle of Palms, S.C. $^1$H NMR spectral data are expressed in ppm relative to internal TMS and were obtained on a Varian Gemini 200 MHz NMR spectrometer. Elemental analyses were carried out by Oneida Research Services Inc. DSC traces were recorded under nitrogen atmosphere on a Perkin Elmer DSC Pyris 1 at heating and cooling rates of 5°/min. UV-Vis absorption spectra were obtained on a Perkin Elmer Lambda 800 Steady State. PL spectra were measured on a SPEX Fluorolog 3 (Model FL3-12); all spectra were corrected for the spectral dispersion of the Xenon lamp, the instrument throughput, the detector response. The excitation wavelength was 365 nm for solutions and 420 nm in case of solid-state samples. For the temperature-dependent PL experiments, a sample was heated between a microscopy slide and a glass cover slip on a Gel Instrumente AG hotstage in connection with a TC2 temperature controller and the PL spectra were measured with the above-mentioned spectrometer by making use of a Y-shaped optical fiber. Polarization microscopy studies were conducted on an Olympus BX60 equipped with a Mettler FP82 hot stage and a Mettler FP80 controller with samples placed between crossed polarizers. Drop-cast films of BCMB and BCMDB were prepared by pipetting solutions of approximately 2.5 mg of the dye in 1 mL of $CHCL_3$ on glass slides, and subsequent evaporation of the solvent under ambient conditions. Blend films of 1 b in i-PP were prepared by guest-diffusion in analogy to the procedures reported before. Thus, a approximately 120 μm thick film of i-PP was produced by melt-pressing 500 mg of i-PP (Polysciences, $\overline{M}_w=220,000$, $\overline{M}_n=40,000$) between two Mylar® foils in a Carver laboratory press at a temperature of 180+ C. and a pressure of 2 tons for 5 min, using a 120 μm spacer. Strips of approximately 7×1 cm of the resulting films were immersed in (a) a solution of BCMDB in $CHCl_3$ (approximately 10 mg/mL) for about 16 h at RT, and (b) a solution of BCMDB in $CHCl_3$ (approximately 30 mg/mL) at 60° C. for about 3 h. The films were subsequently washed with $CHCl_3$ and dried at ambient for 1 h.

Photophysical experiments were conducted on free standing films. Lifetime measurements were made on a PTI Laser Strove Model C720 flurometer, under excitation at 48 lnm and detection at 530 and 650 nm, respectively.

Preparation of BCMB

Terephthaldicarboxyaldehyde (134.1 mg, 1.00 mmol) and (4-methoxyphenyl)acetonitrile (294.4 mg, 2.00 mmol) were dissolved in a mixture of t-BuOH (9 mL) and THF (3 mL) and the mixture was heated to 40-50° C. Potassium t-BuOK (22.4 mg, 0.20 mmol) and n-$Bu_4NH_4OH$ (2 mL of a 1 M solution in MeOH) were added quickly, and a yellow precipitate started to form immediately. The mixture was stirred for 15 min at 50° C., cooled to RT, and poured into acidified methanol (50 mL containing 1 drop of conc. acetic acid). The precipitate was filtered off, excessively washed with MeOH, and dried in vacuo at 50° C. to yield BCMB (351 mg, 90%) in form of yellow crystals.

$^1$H NMR: σ=7.95 (s, 4 H, ArH), 7.64 (d, $^3J_{(H,H)}$=8.9 Hz, 4 H, ArH), 7.44 (s, 2 H, CH=CCN), 6.98 (d, $^3J_{(H,H)}$=8.9 Hz, 4 H, ArH), 3.86 (s, 6 H, O—$CH_3$). Anal. Calcd for $C_{26}H_{20}N_2O_2$: C, 79.57; H, 5.13; N, 7.13. Found: C, 79.51; H, 5.17; N, 7.10

Preparation of BCMDB 1,4-bis-(a-cyano-4-methoxystyryl)-2,5-dimethoxybenxene (1): 2,5-Dimethoxy-terephthalaldehyde (100 mg, 0.510 mmol) and (4-methoxyphenyl)acetonitrile (151.6 mg, 1.02 mmol) were dissolved in a mixture of t-BuOH (9 mL) and THF (3 mL) and the mixture was heated to 40-50° C. t-BuOK (5.7 mg, 0.05 mmol) and n-$Bu_4NH_4OH$ (1 mL of a 1 M solution in methanol) were added quickly, and an orange precipitate started to form immediately. The mixture was stirred for 15 min at 50° C., cooled to RT, and poured into acidified methanol (50 mL containing 1 drop of conc. acetic acid). The precipitate was filtered off, excessively washed with MeOH, and dried in vacuo at 50° C. to yield BCMDB(207 mg, 89%) in form of orange crystals; mp (DSC) 248° C.

$^1$H NMR: σ=7.89, 7.87 (2×s, 2×2 H, ArH+CH=CCN), 7.66 (d, $^3J_{(H,H)}$=8.6 Hz, 4 H, ArH), 7.00 (d, $^3J_{(H,H)}$=8.6 Hz, 4 H, ArH), 3.94 (s, 6 H, O—$CH_3$), 3.87 (s, 6 H, O—$CH_3$). Anal. Calcd for $C_{28}H_{24}N_2O_4$: C, 74.32; H, 5.34; N, 6.19. Found: C, 74.48; H, 5.20; N, 6.24.

Synthesis of (4-(2-Ethylhexyloxy)phenyl)acetonitrile. A suspension of $K_2CO_3$ (4.05 g, 29.2 mmol) and dimethylformamide (15 mL) was purged with Ar for 15 min and heated to 70° C., and $HOPhCH_2CN$ (1.47 g, 11.0 mmol) was added. After 10 min, 2-ethylhexyl bromide (2.75 g, 14.2 mmol) was slowly added via a syringe, and the suspension was stirred at 70° C. under Ar for 4 h. The reaction was subsequently terminated by pouring the suspension into ice-water (150 mL). The aqueous phase was extracted with $CH_2Cl_2$ (3×100 mL). The combined organic layers were washed with $H_2O$ and saturated aqueous NaCl. The organic phase was dried with $MgSO_4$, filtered, and the solvent was evaporated in vacuo. Column chromatography of the resulting crude oil (1.94 g) afforded pure (4-(2-ethylhexyloxy)phenyl)acetonitrile as a slightly yellow oil (0.55 g, 20.4%). $^1$H NMR: σ=7.17 Hz (d, 2 H, ArH), 6.83 Hz (d, 2 H, ArH), 3.85 Hz (d, 2 H, $CH_2$—O), 3.65 Hz (s, 2 H, $CH_2$—CN), 1.7 Hz (m, 1 H, CH), 1.6-1.2 Hz (m, 8 H, $CH_2$), 0.91 Hz (m, 6 H, 2×$CH_3$).

Synthesis of 1,4-Bis-(α-cyano-4-(2-ethylhexyloxystyryl))-2,5-dimethoxy-benzene (BCEDB). 2,5-Dimethoxyterephthaldehyde (120 mg, 0.62 mmol) and (4-(2-ethylhexyloxy)phenyl)acetonitrile (380 mg, 1.55 mmol) were dissolved in a mixture of t-BuOH (11 mL) and THF (3.5 mL) and the mixture was heated to 50° C. t-BuOK (9.8 mg, 0.09 mmol) and n-$Bu_4NH_4OH$ (1 mL of a 1 M solution in methanol) were added quickly, and an orange precipitate started to form immediately. The mixture was stirred for 15 min at 50° C., cooled to RT, and poured into acidified methanol (50 mL containing 1 drop of conc. acetic acid). The precipitate was filtered off, excessively washed with MeOH, and dried in vacuo at 50° C. to yield BCEDB (280 mg, 70%) in form of orange crystals; mp (DSC) 131 and 141° C. $^1$H NMR: σ=7.88 (2×s, 2×2 H, ArH+CH=CCN), 7.63 (d,$^3J_{(H,H)}$=8.6 Hz, 4 H, ArH), 6.96 (d, $^3J_{(H,H)}$=8.6 Hz, 4 H, ArH), 3.95 (s, 6 H, O—$CH_3$), 3.89 (d, 4 H, $^3J_{(H,H)}$=5.3 Hz, O—$CH_2$) 1.7 Hz (m, 2 H, CH), 1.57-1.33 Hz (m, 16 H, $CH_2$), 0.91 Hz (m, 12 H, 4×$CH_3$).

LLDPE

LLDPE samples containing 1.2% (Dowlex BG 2340, ρ=0.942 g/cm$^3$) and 9.3% (Dowlex NG 5056E, ρ=0.919 g/cm$^3$) octene as co-monomer were obtained from Dow.

Preparation of BCMT

Synthesis of 2,5-bis-(α-cyano-4-methoxystyryl)-thiophene (3): Thiophenedicarboxaldehyde (140.2 mg, 1.00 mmol) and (4-methoxyphenyl)acetonitrile (294.4 mg, 2.00 mmol) were dissolved in a mixture of t-BuOH (9 mL) and THF (3 mL) and the mixture was heated to 40-50° C. t-BuOK (22.4 mg, 0.20 mmol) and n-BU$_4$NOH (2 mL of a 1 M solution in MeOH) were added quickly, and a yellow precipitate started to form immediately. The mixture was stirred for 15 min at 50° C., cooled to RT, and poured into acidified methanol (50 mL containing 1 drop of conc. acetic acid). The precipitate was filtered off, excessively washed with MeOH, and dried in vacuo at 50° C. to yield 3 (348 mg, 87%) in form of orange crystals. $^1$H NMR: σ=7.75 (s, 2 H, ArH), 7.60 (d, $^3J_{(H,H)}$=8.6 Hz AA'BB' system, 4 H, ArH), 7.50 (s, 2 H, CH═CCN), 6.97 (d, $^3J_{(H,H)}$=8.9 Hz AA'BB' system, 4 H, ArH), 3.86 (s, 6 H, O—CH$_3$). Anal. Calcd for C$_{24}$H$_{18}$N$_2$O$_2$S (398.485): C, 72.34; H, 4.55; N, 7.03. Found: C, 71.56; H, 4.14; N, 6.80.

Preparation of Films

Blend films of the PL dyes in LLDPE were prepared by guest-diffusion in analogy to the procedures reported before. Thus, films of a thickness of approximately 110 μm were produced by melt-pressing approximately 500 mg of the LLDPE between two Mylar® foils in a Carver laboratory press at a temperature of 180° C. and a pressure of 2 tons for 5 min, using a 110 μm spacer. Strips of approximately 7×1 cm of the resulting films were immersed for usually 16-18 h in (a) a solution of 1, 2, or 3 in CHCl$_3$ (1, 5, 10, or 20 mg/mL) at 60° C. (unless otherwise noted), and (b) a solution of 1, 2, or 3 in toluene (1, 5, 10, or 20 mg/mL) at 70° C. (unless otherwise noted). The films were subsequently washed with CHCl$_3$ (a) or toluene (b) and dried at ambient for at least 1 h. Films were drawn at room temperature in a custom-made stretching frame to draw ratios λ=(I−I$_0$)/I$_0$ of up to 400%, as determined by the displacement of ink-marks printed onto the films.

The invention claimed is:

1. A photoluminescent article, comprising:
   at least one host material; and
   at least one color tunable photoluminescent dye, wherein the emission spectrum of the at least one tunable photoluminescent dye is dependent on the supramolecular architecture of the article.

2. The article of claim 1, wherein a photoluminescent emission spectrum of the dye is capable of being shifted by subjecting the article to mechanical deformation.

3. The article of claim 1, wherein a photoluminescent emission spectrum of the dye is capable of being shifted by subjecting the article to at least one of the stimuli selected from the group comprising mechanical deformation, temperature change, aging of the article, pressure change, and exposure to a chemical compound.

4. The article of claim 1, wherein the color tunable photoluminescent dye is an oligo(phenylene vinylene) compound.

5. The article of claim 4, wherein the oligo(phenylene vinylene) is of the formula:

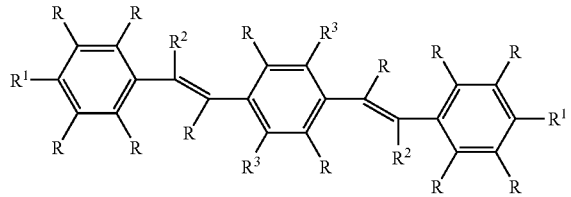

where each R$^2$ may be individually selected from a cyano, halogen, Cl, F, Br, C(═O)R, C(═O)OR, C(═O)NR$_2$, OF$_3$, CN, S(O)$_2$OH, NO$_2$, and N$^+$R$_4$, H, straight chain, branched or cyclic saturated alkyl, alkenyl, or alkynyl, hydroxy alkyl, carboxy alkyl, aryl, or substituted aryl, alkyloxy, methoxy, and ethoxy; and R$^1$, and R$^3$ may be selected from H, straight chain, branched or cyclic saturated alkyl, alkenyl, or alkynyl, hydroxy alkyl, carboxy alkyl, aryl, or substituted aryl, alkyloxy, methoxy, ethoxy, cyano, halogen, Cl, F, Br, C(═O)R, C(═O)OR, C(═O)NR$_2$, CF$_3$, CN, S(O)$_2$OH, NO$_2$, and N$^+$R$_4$.

6. The article of claim 5, wherein each R is independently selected from H, straight chain, branched or cyclic saturated alkyl, alkenyl, or alkynyl, hydroxy alkyl, carboxy alkyl, aryl, or substituted aryl, methoxy, and ethoxy.

7. The article of claim 1, wherein a portion of the color tunable photoluminescent dye forms excimers, wherein the excimers emit a different emission spectrum than a portion of the color tunable photoluminescent dye not forming an excimer.

8. The article of claim 7, wherein the ratio of the portion of the photoluminescent dye forming excimers to the portion of the photoluminescent dye not forming an excimer depends on the supramolecular architecture the photoluminescent dye in the article.

9. The article of claim 1, further comprising a solvent.

10. The article of claim 1, wherein the solvent at least one of ethers, cyclic ethers, C$_5$-C$_{10}$ alkanes, C$_5$-C$_8$ cycloalkanes which may be substituted with from 1 to 3 C$_1$-C$_4$ alkyl groups, aromatic hydrocarbon solvents, such as toluene, halogenated hydrocarbon solvents, such as trichloromethane, acetonitrile, dimethylformamide, mixtures of such solvents, and supercritical solvents, CO$_2$, C$_1$-C$_4$ alkanes in which any H may be replaced with F, compounds of the formula R$_4$ OR$_5$, in which each of R$_4$ and R$_5$ is independently an alkyl group of from 1 to 6 carbon atoms which may be further substituted with a C$_1$-C$_4$- alkoxy group, when one of R$_4$ and R$_5$ is methyl, the other of R$_4$ and R$_5$ is alkyl of from 4 to 6 carbon atoms or C$_1$-C$_4$-alkoxyethyl, diethyl ether, diphenyl ether, ethyl propyl ether, dipropyl ether, methyl t-butyl ether, di-t-butyl ether, dimethoxyethane, diethylene glycol dimethyl ether, cyclic ethers, THF, dioxane, aromatic hydrocarbon solvents, benzene, toluene, o-xylene, m-xylene, p-xylene, any isomer or mixture of isomers of cumene, halogenated hydrocarbon solvents, CH$_2$Cl$_2$, CHCl$_3$, 1,2-dichloroethane and benzene substituted from 1 to 6 times with fluorine and/or chlorine.

11. A material, comprising:
    at least one host material; and
    at least one color tunable photoluminescent dye, wherein the emission spectrum of the at least one tunable photoluminescent dye is dependent on the supramolecular architecture of the material.

12. The material of claim 11, wherein a photoluminescent emission spectrum of the dye is capable of being shifted by subjecting the article to at least one of a mechanical deformation, a temperature change, aging of the article, a pressure change, or exposure to a chemical compound.

13. The material of claim 11, wherein the color tunable photoluminescent dye is an oligo(phenylene vinylene) compound.

14. The material of claim 13, wherein the oligo(phenylene vinylene) is of the formula:

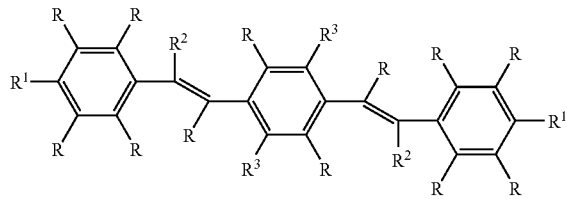

where each $R^2$ may be individually selected from a cyano, halogen, Cl, F, Br, C(=O)R, C(=O)OR, C(=O)NR$_2$, CF$_3$, CN, S(O)$_2$OH, NO$_2$, and N$^+$R$_4$; and $R^1$, and $R^3$ may be selected from H, straight chain, branched or cyclic saturated alkyl, alkenyl, or alkynyl, hydroxy alkyl, carboxy alkyl, aryl, or substituted aryl, methoxy, and ethoxy.

15. The material of claim 14, wherein each R is independently selected from H, straight chain, branched or cyclic saturated alkyl, alkenyl, or alkynyl, hydroxy alkyl, carboxy alkyl, aryl, or substituted aryl, methoxy, and ethoxy.

16. The material of claim 11, wherein a portion of the color tunable photoluminescent dye forms excimers, wherein the excimers emit a different emission spectrum than a portion of the photoluminescent dye not forming an excimer.

17. The material of claim 16, wherein the ratio of the portion of the photoluminescent dye forming excimer to the portion of the photoluminescent dye not forming an excimer depends on the supramolecular architecture the photoluminescent dye in the article.

18. The material of claim 11, further comprising a solvent.

19. The material of claim 11, wherein the solvent at least one of ethers, cyclic ethers, C$_5$-C$_{10}$ alkanes, C$_5$-C$_8$ cycloalkanes which may be substituted with from 1 to 3 C$_1$-C$_4$ alkyl groups, aromatic hydrocarbon solvents, such as toluene, halogenated hydrocarbon solvents, such as trichloromethane, acetonitrile, dimethylformamide, mixtures of such solvents, and supercritical solvents, CO$_2$, C$_1$-C$_4$ alkanes in which any H may be replaced with F, compounds of the formula R$_4$ OR$_5$, in which each of R$_4$ and R$_5$ is independently an alkyl group of from 1 to 6 carbon atoms which may be further substituted with a C$_1$-C$_4$-alkoxy group, when one of R$_4$ and R$_5$ is methyl, the other of R$_4$ and R$_5$ is alkyl of from 4 to 6 carbon atoms or C$_1$-C$_4$-alkoxyethyl, diethyl ether, diphenyl ether, ethyl propyl ether, dipropyl ether, methyl t-butyl ether, di-t-butyl ether, dimethoxyethane, diethylene glycol dimethyl ether, cyclic ethers, THF, dioxane, aromatic hydrocarbon solvents, benzene, toluene, o-xylene, m-xylene, p-xylene, any isomer or mixture of isomers of cumene, halogenated hydrocarbon solvents, CH$_2$Cl$_2$, CHCl$_3$, 1,2-dichloroethane and benzene substituted from 1 to 6 times with fluorine and/or chlorine.

20. A photoluminescent dye of the formula:

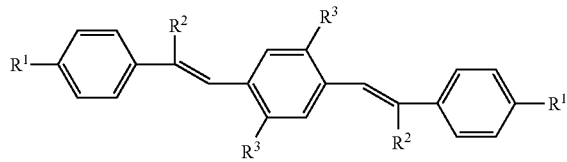

where $R^2$ is an cyano, halogen, Cl, F, Br, C(=O)R, C(=O)OR, C(=O)NR$_2$, CF$_3$, CN, S(O)$_2$OH, NO$_2$, and N$^+$R$_4$, R$^1$ is alkoxy, methoxy, ethoxy group and R$^3$ may be any group which affects the desired physical or electronic properties of the compound selected from H, straight chain, branched or cyclic saturated alkyl, alkenyl, or alkynyl, hydroxy alkyl, carboxy alkyl, aryl, or substituted aryl, alkoxy, methoxy, and ethoxy.

21. The photoluminescent dye of claim 20, wherein the photoluminescent dye is one of 1,4-Bis-(α-cyano-4-methoxystyryl)-benzene, 1,4-bis-(α-cyano-4-methoxystyryl)-2,5-dimethoxybenzene, and 1,4-bis-(α-cyano-4-(2-ethylhexyloxystyryl) -2,5-dimethoxybenzene and 2,5-bis-(α-cyano-4-methoxystyryl) -thiophene.

22. A method of determining a degree of mechanical deformation, a temperature change, aging of the article, a pressure change, exposure to a chemical compound on an article, comprising:
measuring the photoluminescent emission spectra of an article comprising at least one host material and at least one color tunable photoluminescent dye, wherein the emission spectrum of the at least one tunable photoluminescent dye is dependent on the supramolecular architecture of the material; and
comparing the photoluminescent emission spectrum of the article with the photoluminescent emission spectrum prior to the mechanical deformation, a temperature change, aging of the article, a pressure change, or exposure to a chemical compound.

23. The method of claim 22, wherein measuring the photoluminescent spectrum comprises visually inspecting the article.

24. The article of claim 1, wherein a difference between a maximum of the emission spectrum of the color tunable photoluminescent dye for a crystalline solid of the color tunable photoluminescent dye to a maximum of the emission spectrum for the molecular liquid solution is greater than 50 nm.

25. The article of claim 7, wherein a ratio of the photoluminescence intensity of the excimer portion to the photoluminescence intensity of portion not in an excimer is capable of changing by a factor of at least 3 after the article is subjected to at least one of mechanical deformation, temperature change, aging of the article, pressure change, and exposure to a chemical compound.

26. The article of claim 1, wherein the host material comprises a polymer.

27. The article of claim 26, wherein the polymer is at least one material selected from a polyolefin, polyethylene, linear low density polyethylene, low density polyethylene, high density polyethylene, ultra high molecular weight polyethylene, poly(propylene), cyclic olefin polymers and copolymers, poly(acrylate)s, polymethyl methacrylate, poly methacrylate, polybutyl acrylate, poly(acrylamide), poly (acrylonitrile), vinyl polymers, poly(vinylchloride), poly (vinylidenechloride), poly(vinylfluoride), poly (tetrafluoroethylene), poly(chlorotrifluoroethylene), poly (vinylacetate), poly(vinylalcohol), poly(2-vinylpyridine), poly(vinyl butyral), poly(styrene)s, copolymers, acrylonitrile butadiene styrene copolymer, ethylene vinyl acetate copolymers, polyamides, polyamide 6,6,6, polyamide 12, polyamide 4,6, polyesters, poly(ethylene terephthalate), poly(butylene terephthalate), poly(ethylene naphthalate), poly(carbonate)s, polyurethanes, poly(aryl sulfones), poly (phenyleneoxide), thermoset resins, phenol formaldehyde resins, resoles, novolacs, epoxy resins, regenerated cellulose, cellophane, cellulose acetate, cellulose acetate butyrate, natural fibers, wool, silk, cotton, ramie, jute, starch-based materials, styrene-butadiene copolymers, polybutadiene, ethylene-propylene copolymers, polychloroprene, polyisoprene, nitrile rubbers, silicone rubbers, or thermoplastic elastomers.

* * * * *